(12) United States Patent
Solum et al.

(10) Patent No.: US 11,716,580 B2
(45) Date of Patent: Aug. 1, 2023

(54) HEALTH MONITORING WITH EAR-WEARABLE DEVICES AND ACCESSORY DEVICES

(71) Applicant: STARKEY LABORATORIES, INC., Eden Prairie, MN (US)

(72) Inventors: Jeffrey Paul Solum, Greenwood, MN (US); Gregory John Haubrich, Champlin, MN (US)

(73) Assignee: STARKEY LABORATORIES, INC., Eden Prairie, MN (US)

( * ) Notice: Subject to any disclaimer, the term of this patent is extended or adjusted under 35 U.S.C. 154(b) by 0 days.

(21) Appl. No.: 17/860,366

(22) Filed: Jul. 8, 2022

(65) Prior Publication Data

US 2022/0345836 A1  Oct. 27, 2022

Related U.S. Application Data

(63) Continuation of application No. 17/188,623, filed on Mar. 1, 2021, now Pat. No. 11,395,076, which is a
(Continued)

(51) Int. Cl.
*H04R 1/02* (2006.01)
*H04R 25/00* (2006.01)
(Continued)

(52) U.S. Cl.
CPC ............. *H04R 25/554* (2013.01); *A61B 5/01* (2013.01); *A61B 5/4815* (2013.01);
(Continued)

(58) Field of Classification Search
CPC .. H04R 25/554; H04R 2225/025; A61B 5/01; A61B 5/4815; A61B 5/6803;
(Continued)

(56) References Cited

U.S. PATENT DOCUMENTS 5,204,917 A  4/1993 Arndt et al.
5,253,300 A  10/1993 Knapp
(Continued)

FOREIGN PATENT DOCUMENTS

DE  8804743  9/1989
DE  102009033898  11/2010
(Continued)

OTHER PUBLICATIONS

Amendment in Response to Office Action dated Jul. 12, 2019, from U.S. Appl. No. 16/135,829, filed Jul. 12, 2019, 11 pp.
(Continued)

*Primary Examiner* — Ammar T Hamid
(74) *Attorney, Agent, or Firm* — Mueting Raasch Group

(57) ABSTRACT

Each accessory device in a set of accessory devices may establish a respective communication link between the accessory device and an ear-wearable device. A particular accessory device in the set of accessory devices may receive data via the communication link between the particular accessory device and the ear-wearable device. The data comprise information generated based on sensor signals from sensors that monitor a user of the ear-wearable device. The accessory devices perform a health monitoring activity based on the data.

20 Claims, 6 Drawing Sheets

Related U.S. Application Data continuation of application No. 16/289,078, filed on Feb. 28, 2019, now Pat. No. 10,939,216, which is a continuation-in-part of application No. 16/135,829, filed on Sep. 19, 2018, now abandoned, and a continuation-in-part of application No. 16/135,784, filed on Sep. 19, 2018, now Pat. No. 10,728,642, and a continuation-in-part of application No. 16/135,867, filed on Sep. 19, 2018, now Pat. No. 11,019,417, and a continuation-in-part of application No. 16/135,712, filed on Sep. 19, 2018, now Pat. No. 10,659,859.

(60) Provisional application No. 62/636,551, filed on Feb. 28, 2018.

(51) Int. Cl.
| | | |
|---|---|---|
| *A61B 5/00* | (2006.01) | |
| *A61B 5/01* | (2006.01) | |
| *A61B 5/024* | (2006.01) | |
| *A61B 5/0205* | (2006.01) | |

(52) U.S. Cl.
CPC ........ *A61B 5/6803* (2013.01); *A61B 5/02055* (2013.01); *A61B 5/02427* (2013.01); *A61B 5/02438* (2013.01); *A61B 5/6815* (2013.01); *A61B 2562/0219* (2013.01); *H04R 2225/025* (2013.01)

(58) Field of Classification Search
CPC ............ A61B 5/02055; A61B 5/02427; A61B 5/02438; A61B 5/6815; A61B 2562/0219
USPC .................................................. 381/87, 334
See application file for complete search history.

(56) References Cited

U.S. PATENT DOCUMENTS

| | | |
|---|---|---|
| 5,565,759 A | 10/1996 | Dunstan |
| 7,106,877 B1 | 9/2006 | Linville |
| 7,110,562 B1 | 9/2006 | Feeley et al. |
| 7,151,839 B2 | 12/2006 | Niederdraenk |
| 7,565,179 B2 | 7/2009 | Hyatt |
| 8,169,938 B2 | 5/2012 | Duchscher et al. |
| 8,795,684 B2 | 8/2014 | Cichon |
| 8,798,294 B2 | 8/2014 | Havenith et al. |
| 8,848,958 B2 | 9/2014 | Karlsen |
| 9,014,405 B2 | 4/2015 | Larsen et al. |
| 9,124,994 B2 | 9/2015 | Corti et al. |
| 9,338,561 B2 | 5/2016 | Gran et al. |
| 9,380,106 B2 | 6/2016 | Payne et al. |
| 9,380,394 B2 | 6/2016 | Krystek et al. |
| 9,543,778 B1 | 1/2017 | Corti |
| 9,788,130 B2 | 10/2017 | Müller |
| 9,900,680 B2 | 2/2018 | Milam et al. |
| 9,943,746 B2 | 4/2018 | Kennard et al. |
| 9,980,033 B2 | 5/2018 | Boesen |
| 10,306,381 B2 | 5/2019 | Sandhu et al. |
| 10,516,281 B2 | 12/2019 | Dennis |
| 10,939,216 B2 | 3/2021 | Solum et al. |
| 2009/0262964 A1 | 10/2009 | Havenith et al. |
| 2012/0041517 A1 | 2/2012 | Walsh et al. |
| 2012/0140963 A1 | 6/2012 | Larsen et al. |
| 2013/0034584 A1 | 2/2013 | Cichon |
| 2013/0294627 A1 | 11/2013 | Karlsen |
| 2013/0343584 A1 | 12/2013 | Bennett et al. |
| 2013/0343585 A1* | 12/2013 | Bennett .................. H04W 4/80 381/317 |
| 2014/0156775 A1 | 6/2014 | Payne et al. |
| 2014/0254845 A1 | 9/2014 | Hastrup |
| 2015/0036835 A1 | 2/2015 | Chen |
| 2015/0181357 A1 | 6/2015 | Krystek et al. |
| 2015/0341730 A1 | 11/2015 | Pedersen et al. |
| 2015/0350797 A1 | 12/2015 | Müller |
| 2016/0006292 A1 | 1/2016 | Hatanaka et al. |
| 2016/0058093 A1 | 3/2016 | Kennard et al. |
| 2016/0100261 A1 | 4/2016 | Shennib |
| 2017/0064429 A1 | 3/2017 | Hirsch et al. |
| 2017/0094390 A1 | 3/2017 | Chawan et al. |
| 2017/0195804 A1 | 7/2017 | Sandhu et al. |
| 2017/0289711 A1 | 10/2017 | Maas |
| 2018/0014109 A1 | 1/2018 | Boesen |
| 2018/0020295 A1 | 1/2018 | Pander et al. |
| 2018/0072343 A1 | 3/2018 | Sugita et al. |
| 2018/0116560 A1 | 5/2018 | Quinn et al. |
| 2018/0124491 A1 | 5/2018 | Dragicevic et al. |
| 2019/0246216 A1 | 8/2019 | Frederiksen et al. |

FOREIGN PATENT DOCUMENTS

| | | |
|---|---|---|
| EP | 2849462 | 3/2015 |
| EP | 3035710 | 11/2016 |
| EP | 3101917 | 12/2016 |

OTHER PUBLICATIONS

Cho et al., "A 10.8 mW Body Channel Communications/MIGS Dual-Band Transceiver for a Unified Body Sensor Network Controller," IEEE Journal of Solid-Slate Circuits, vol. 44, No. 12, Dec. 2009, pp. 3459-3468.

Hao et al., "Wireless body sensor networks for health-monitoring applications," Physiological Measurement, vol. 29, ~o. 11, Nov. 2008., 42 pp.

International Search Report and Written Opinion of International Application No. PCT/US2019/019649, dated Jul. 5, 2019, 19 pp.

International Search Report and Written Opinion of International Application No. PCT/US2019/019653, dated May 3, 2019, 13 pp.

International Search Report and Written Opinion of International Application No. PCT/US2019/019657, dated Jun. 16, 2019, 16 pp.

International Search Report and Written Opinion of International Application No. PCT/US2019/019659, dated Jun. 24, 2019, 18 pp.

Invitation to Restrict or Pay Additional Fees, from International Application No. PCT/US2019/019649, mailed May 3, 2019, 14 pp.

Invitation to Restrict or Pay Additional Fees, from International Application No. PCT/US2019/019657, mailed Apr. 30, 2019, 11 pp.

Invitation to Restrict or Pay Additional Fees, from International Application No. PCT/US2019/019657, mailed Apr. 30, J019, 11 pp.

Invitation to Restrict or Pay Additional Fees, from International Application No. PCT/US2019/019659, mailed Apr. 29, 2019, 12 pp.

Majumder et al., "Wearable Sensors for Remote Health Monitoring," Sensors, vol. 1, No. 130, Jan. 12, 2017, 45 PP.

U.S. Appl. No. 16/135,712, filed Sep. 19, 2018, by Solum et al.
U.S. Appl. No. 16/135,784, filed Sep. 19, 2018, by Solum et al.
U.S. Appl. No. 16/135,829, filed Sep. 19, 2018, by Solum et al.
U.S. Appl. No. 16/135,867, filed Sep. 19, 2018, by Solum et al.

* cited by examiner

HEALTH MONITORING WITH EAR-WEARABLE DEVICES AND ACCESSORY DEVICES

This application is a continuation of U.S. patent application Ser. No. 17/188,623, filed Mar. 1, 2021, which is a continuation of U.S. patent application Ser. No. 16/289,078, filed Feb. 28, 2019, now U.S. Pat. No. 10,939,216, which is a continuation-in-part of U.S. patent application Ser. No. 16/135,712, filed Sep. 19, 2018, now U.S. Pat. No. 10,659,859, a continuation-in-part of U.S. patent application Ser. No. 16/135,784, filed Sep. 19, 2018, now U.S. Pat. No. 10,728,642, a continuation-in-part of U.S. patent application Ser. No. 16/135,829, filed Sep. 19, 2018, a continuation-in-part of U.S. patent application Ser. No. 16/135,867, filed Sep. 19, 2018, now U.S. Pat. No. 11,019,417, each of which claims the benefit of U.S. Provisional Application No. 62/636,551, filed Feb. 28, 2018, the entire content of each of which is hereby incorporated by reference.

TECHNICAL FIELD

This disclosure relates to ear-wearable devices and accessories for ear-wearable devices.

BACKGROUND

Ear-wearable devices are devices designed to be worn on, in, or near one or more of a user's ears. Common types of ear-wearable devices include hearing assistance devices (e.g., "hearing aids" and "hearing instruments"), earbuds, headphones, hearables, cochlear implants, and so on. In some examples, an ear-wearable device may be implanted or osseointegrated into a user. Some ear-wearable devices include additional features beyond just environmental sound-amplification. For example, some modern ear-wearable devices include advanced audio processing for improved device functionality, controlling and programming the devices, and beamforming, and some can even communicate wirelessly with external devices including other hearing aids (e.g., for streaming media).

SUMMARY

In general, this disclosure describes techniques for health monitoring that involve ear-wearable devices and devices that act as accessories to ear-wearable devices. For instance, in one example, this disclosure describes a method of health monitoring, the method comprising: establishing, by each accessory device in a set of accessory devices, a respective communication link between the accessory device and an ear-wearable device, the respective communication link being a wireless communication link in which the accessory device receives radio signals generated by the ear-wearable device, an optical communication channel in which the accessory device receives light generated by the ear-wearable device, or an electrical communication channel in which the accessory device receives electrical pulses generated by the ear-wearable device; receiving, by a particular accessory device in the set of accessory devices, first data via the communication link between the particular accessory device and the ear-wearable device, the first data comprising information generated based on sensor signals from sensors that monitor a user of the ear-wearable device; and performing, by the set of accessory devices, a health monitoring activity based on the first data.

In another example, this disclosure describes a method comprising: obtaining, by the ear-wearable device, sensor data from one or more sensors configured to gather information about a user of the ear-wearable device; determining, by the ear-wearable device, based on the sensor data, whether the user has experienced an acute health event; in response to determining that the user has experienced an acute health event: establishing, by the ear-wearable device, a communication link between the ear-wearable device and a first accessory device, the communication link being a wireless communication link in which the accessory device receives wireless signals generated by the ear-wearable device; and sending, by the ear-wearable device, first health data to the first accessory device via the communication link, the first health data being based on the sensor data; and in response to determining subsequently that the user has not experienced the acute health event, sending, by the ear-wearable device, second health data based on the sensor data to a second accessory device while the ear-wearable device is coupled to a charging device that charges a power source of the ear-wearable device.

In one example, this disclosure describes a method of health monitoring, the method comprising: establishing, by each accessory device in a set of accessory devices, a respective communication link between the accessory device and an ear-wearable device, the respective communication link being: a wireless communication link in which the accessory device receives radio signals generated by the ear-wearable device, an optical communication channel in which the accessory device receives light generated by the ear-wearable device, or an electrical communication channel in which the accessory device receives electrical pulses generated by the ear-wearable device; receiving, by a particular accessory device in the set of accessory devices, first data via the communication link between the particular accessory device and the ear-wearable device, the first data comprising information generated based on sensor signals from sensors that monitor a user of the ear-wearable device; and performing, by the set of accessory devices, a health monitoring activity based on the first data.

In another example, this disclosure describes an accessory device comprising: one or more communication units configured to: establish a communication link between the accessory device and an ear-wearable device, the communication link being: a wireless communication link in which the accessory device receives radio signals generated by the ear-wearable device, an optical communication channel in which the accessory device receives light generated by the ear-wearable device, or an electrical communication channel in which the accessory device receives electrical pulses generated by the ear-wearable device; and receive first data via the communication link between the accessory device and the ear-wearable device, the first data comprising information generated based on sensor signals from sensors that monitor a user of the ear-wearable device; and one or more processors configured to perform a health monitoring activity based on the first data.

In another example, this disclosure describes an accessory device comprising: means for establishing a communication link between the accessory device and an ear-wearable device, the communication link being a wireless communication link in which the accessory device receives radio signals generated by the ear-wearable device, an optical communication channel in which the accessory device receives light generated by the ear-wearable device, or an electrical communication channel in which the accessory device receives electrical pulses generated by the ear-wearable device; means for receiving first data via the communication link between the accessory device and the ear-wearable device, the first data comprising information generated based on sensor signals from sensors that monitor a user of the ear-wearable device; and means for performing a health monitoring activity based on the first data.

In another example, this disclosure describes a computer-readable storage medium having instructions that cause a set of accessory devices to: establish, by each accessory device in the set of accessory devices, a respective communication link between the accessory device and an ear-wearable device, the respective communication link being: a wireless communication link in which the accessory device receives radio signals generated by the ear-wearable device, an optical communication channel in which the accessory device receives light generated by the ear-wearable device, or an electrical communication channel in which the accessory device receives electrical pulses generated by the ear-wearable device; receive, by a particular accessory device in the set of accessory devices, first data via the communication link between the particular accessory device and the ear-wearable device, the first data comprising information generated based on sensor signals from sensors that monitor a user of the ear-wearable device; and perform, by the set of accessory devices, a health monitoring activity based on the first data.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
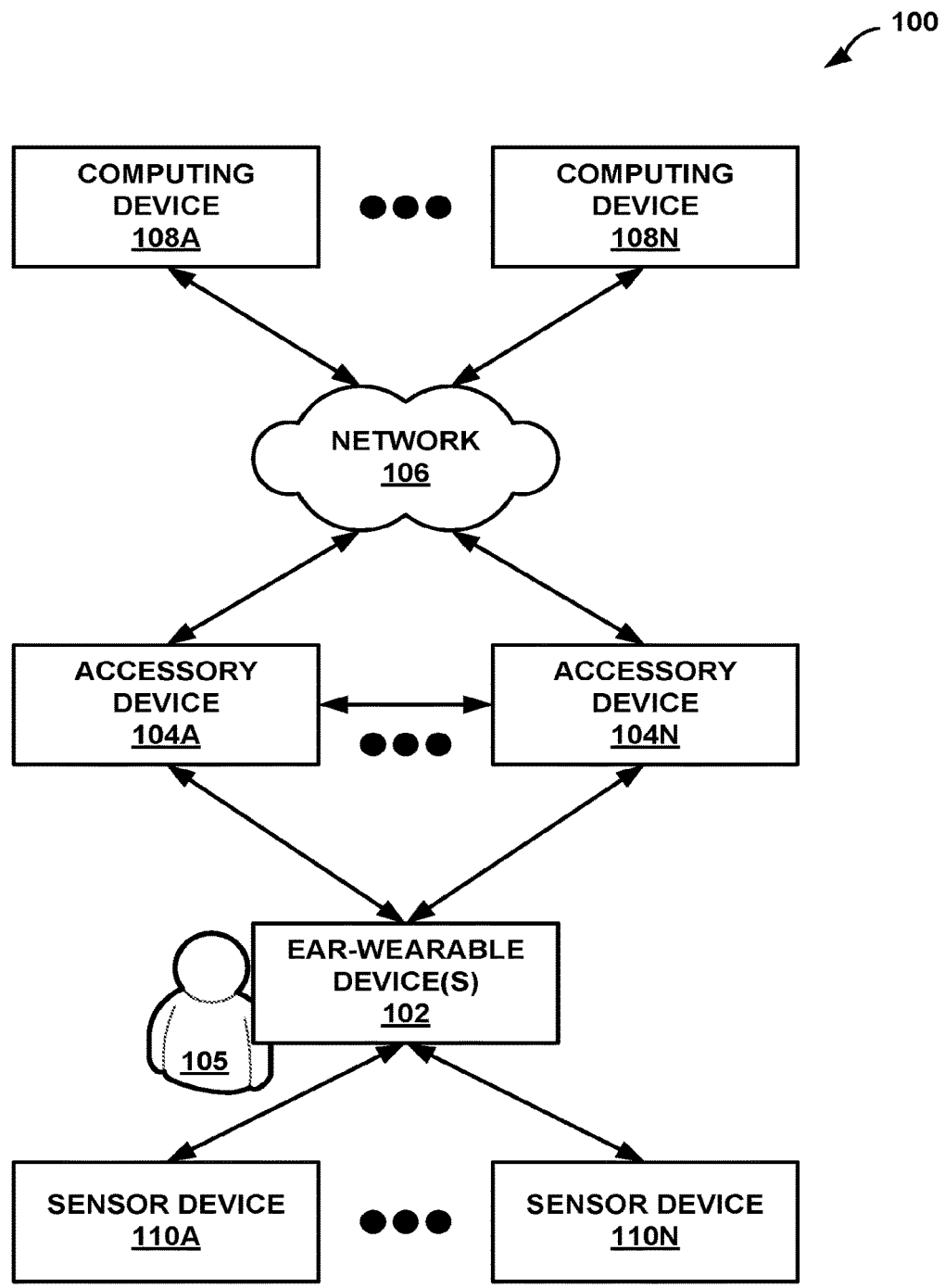
FIG. 1 is a block diagram illustrating an example health monitoring system in accordance with one or more aspects of the present disclosure.

An ear-wearable device may include one or more sensors that gather data about a user of the ear-wearable device. For example, the ear-wearable device may include a heart rate sensor, a photoplethysmography sensor, an inertial measurement unit (IMU), a temperature sensor, a pressure sensor, magnetic field sensors, and so on. The data gathered by such sensors may be used to perform health monitoring activities that track various aspects of the health of the user. For example, the data gathered by such sensors may be used by a health monitoring service in health monitoring activities, such as determining whether the user has fallen, whether the user is performing a sufficient amount of exercise, whether the user has a fever, whether the user is experiencing loneliness or depression, whether the user is experiencing tremors, whether the user is experiencing or about to experience a seizure, whether the user's blood glucose is under control, whether the user has a cardiac arrhythmia, and so on.

Various types of users may benefit from health monitoring services. For example, patients under the care of a physician may have chronic disease states which require monitoring by physicians/healthcare professionals. Furthermore, certain people may be identified as being at high-risk for a life-threatening medical episode based on health, or family history. Additionally, a user of a hearing device may want the added security of having key real-time heath-status indicators measured and/or monitored.

The processes required to perform activities of a health monitoring service may require significant amounts of power and computational resources. Because ear-wearable devices are typically designed to be as small as possible, the power sources of ear-wearable devices are commensurately small. Moreover, the computations required to perform activities of a health monitoring service may require the use of complex processing circuits, which may add size and cost to the ear-wearable devices. Thus, performing certain activities of a health monitoring service on an ear-wearable device may be impractical.

As described in this disclosure, a health monitoring system may be implemented that uses one or more accessory devices as support nodes for a set of one or more ear-wearable devices worn by a user. As such, the accessory devices may perform communication and processing activities on behalf of the ear-wearable devices. For instance, the ear-wearable devices may transmit data gathered by sensors to one or more of the accessory devices. The accessory devices may support health monitoring activities by processing the data, retransmitting the data to one or more remote computing systems, or a combination thereof.

The accessory devices may include devices that are specifically designed for use as accessories to the ear-wearable devices. For instance, the accessory devices may include a charging device configured for recharging power sources of the ear-wearable devices. In another example, the accessory devices may include media streamer devices that receive media data from one or more source devices and wirelessly transmit the media data to the ear-wearable devices. The use of such accessory devices as support nodes for the ear-wearable devices may increase the ability of the ear-wearable devices to offload data for processing in a health monitoring system. In this way, a system that includes accessory devices and ear-wearable devices may support health monitoring activities without unduly increasing a computational load of the ear-wearable devices.

FIG. 1 is a block diagram illustrating an example health monitoring system 100, in accordance with one or more aspects of the present disclosure. In the example of FIG. 1, health monitoring system 100 includes a set of one or more ear-wearable device(s) 102, a set of one or more accessory devices 104A through 104N (collectively, "accessory devices 104"), a network 106, and a set of one or more computing devices 108A through 108N (collectively, "computing devices 108"). Additionally, health monitoring system 100 may include a set of one or more sensor devices 110A through 110N (collectively, "sensor devices 110"). In other examples of this disclosure, health monitoring system 100 may include more, fewer, or different devices, systems, or components. For instance, in some examples, health monitoring system 100 does not include computing devices 108, network 106, and/or sensor devices 110.

Each of ear-wearable device(s) 102 may be a device designed for wear at, on, or near an ear of a user 105. User 105 may wear a single ear-wearable device or may concurrently wear multiple ear-wearable devices. Ear-wearable device(s) 102 may comprise one or more of various types of devices configured to provide hearing assistance. For example, ear-wearable device(s) 102 may comprise one or more hearing assistance devices. In another example, ear-wearable device(s) 102 may comprise one or more Personal Sound Amplification Products (PSAPs). In another example, ear-wearable device(s) 102 may comprise one or more cochlear implants, cochlear implant magnets, cochlear implant transducers, and cochlear implant processors. In another example, ear-wearable device(s) 102 may comprise one or more so-called "hearables" that provide various types of functionality. In other examples, ear-wearable device(s) 102 may comprise other types of devices that are wearable in, on, or in the vicinity of the ears of user 105. In other examples, ear-wearable device(s) 102 may comprise other types of devices that are implanted or otherwise osseointegrated with the skull of user 105; wherein the ear-wearable device is able to facilitate stimulation of the ears of user 105 via the bone conduction pathway.

In examples where ear-wearable device(s) 102 include one or more hearing assistance devices, health monitoring system 100 may be referred to as a hearing assistance system. In examples where ear-wearable device(s) 102 are hearing-assistance devices, ear-wearable device(s) 102 may be primarily configured to provide sound to user 105 for hearing. In some instances, such as when user 105 has unilateral hearing loss, user 105 may wear a single hearing-assistance device. In other instances, such as when user 105 has with bilateral hearing loss, user 105 may wear two hearing-assistance devices, with one hearing-assistance device for each ear of user 105.

In general, there are three types of hearing-assistance devices. A first type of hearing-assistance devices includes a housing or shell that is designed to be worn in the ear for both aesthetic and functional reasons and enclose the electronic components of the hearing instrument. Such hearing-assistance devices may be referred to as in-the-ear (ITE), in-the-canal (ITC), completely-in-the-canal (CIC), or invisible-in-the-canal (IIC) hearing assistance devices. Some in-the-ear hearing assistance devices instruments have limited capabilities due to their small size and limited volume for housing electronics and power sources. Examples of drawbacks of IIC devices include a shortened battery life, lower fit rates due to the volume of components to be placed in the canal, lack of wireless features like programming and audio streaming, no telecoil, and patient frustration with changing batteries. A second type of hearing-assistance devices, referred to as behind-the-ear (BTE) hearing-assistance devices, include a housing worn behind the ear contains all of the electronic components of the hearing instrument, including the receiver (i.e., the speaker). The receiver conducts sound to an earbud inside the ear via an audio tube. Lastly, a third type of hearing-assistance devices, referred to as a receiver-in-canal (MC) hearing-assistance devices, has a housing worn behind the ear that contains all of the electronic components except for the receiver, which is worn in the ear canal. The output state of a RIC hearing instrument may be electrically connected to the receiver worn in the ear canal.

Accessory devices 104 may include devices that are configured for use with ear-wearable device(s) 102. Example types of accessory devices 104 may include charging cases for ear-wearable device(s) 102, storage cases for ear-wearable device(s) 102, media streamer devices, phone streamer devices smart televisions, smart speaker devices, medical alarm devices, key fobs, smartwatches, smartphones, motion or presence sensor devices, smart displays, screen-enhanced smart speakers, wireless routers, wireless communication hubs, prosthetic devices, mobility devices, remote microphones, remote controls for ear-wearable device(s) 102 special-purpose devices, and other types of devices. In some examples, accessory device 104 include devices that are specifically designed to be used as accessories of ear-wearable device(s) 102. In some examples, one or more of ear-wearable device(s) 102 and/or accessory devices 104 may be equipped with a virtual personal assistant, such as ALEXA™ from Amazon.com, Inc. or GOOGLE ASSISTANT™ from Google LLC. References in this disclosure to accessory devices 104 performing particular actions may refer to one of accessory devices 104 performing the particular actions or two or more of accessory devices 104 performing the particular actions.

Each of accessory devices 104 may be configured to establish a respective communication link between the accessory device and ear-wearable device(s) 102. Such communication links may or may not occur concurrently with each other. Moreover, the communication link between an accessory device and ear-wearable device(s) 102 may be established and disestablished multiple times. In examples where there are multiple ear-wearable device(s) 102, a communication link between an accessory device and ear-wearable device(s) 102 may in fact be a communication link solely between the accessory device and one of ear-wearable device(s) 102.

In some examples, the communication link between an accessory device and ear-wearable device(s) 102 is a wireless communication link in which the accessory device receives radio signals generated by ear-wearable device(s) 102. In some examples, the communication link between an accessory device and ear-wearable device(s) 102 is an optical communication channel in which the accessory device receives light generated by the ear-wearable device. In some example, the communication link between an accessory device and ear-wearable device(s) is an electrical communication channel in which the accessory device receives electrical pulses generated by the ear-wearable device. In such examples, the communication channel does not involve any intermediate devices, such as network routers or gateways.

In the example of FIG. 1, network 106 includes a communication network that enables communication between one or more of accessory devices 104 and one or more of computing devices 108. Network 106 may include a variety of different types of communication networks. For example, network 106 may include one or more local area networks, wide area networks, the Internet, a cellular data network, or other types of networks. Network 106 may include wired and/or wireless communication links. In some examples, network 106 represents any public or private communications network, for transmitting data between computing systems and computing devices. Network 106 may include a cellular communication network, such as a 3G network, 4G LTE network, a 5G network, or other cellular communication network using another type of wireless communication technology. Network 106 may include a short-range communication network, such as Bluetooth®, Wi-Fi®, or other type of communication network including direct-connections, such as Wi-Fi® direct and inferred direct communication networks. Network 106 may include or be communicatively coupled to the Internet or other types of networks, both personal and private. Network 106 may include one or more network hubs, network switches, network routers, or any other network equipment, that are operatively inter-coupled thereby providing for the exchange of information between components of health monitoring system 100. One or more of accessory devices 104 and computing devices 108 may each be operatively coupled to network 106 using respective network links. The links coupling accessory devices 104 and computing devices 108 to network 106 may be Ethernet or other types of network connections; such connections may be wireless and/or wired connections.

Computing devices 108 may include various types of computing devices. For example, computing devices 108 may include server devices, smartphones, personal computers, tablet computers, wireless base stations, other ear-wearable devices, and so on. In some examples, one or more of computing devices 108 include devices used by third parties, such as healthcare professionals, family members, other ear-wearable device users, and other types of individuals. This disclosure may refer to a party other than user 105 as a third party.

Each of computing devices 108 may include a single electronic computing device or combination of two or more electronic computing devices, and may include: a hearing assistance device programmer (e.g., a device used by a medical professional to calibrate, change parameters, or otherwise configure ear-wearable device(s) 102, sensor devices 110, and/or accessory devices 104 according to a treatment plan or treatment protocol), one or more mobile computing devices (e.g., a mobile phone, laptop computer, tablet computer, automobile computer, or other mobile device), one or more wearable computing devices (e.g., a computerized watch, computerized glasses, and the like), one or more server devices, one or more server blades, one or more personal computers, one or more content delivery network devices, and any other types of mobile, non-mobile, or wearable computing devices. Thus, in general, descriptions in this disclosure of computing devices 108 performing particular actions may be interpreted as some combination of one or more mobile, non-mobile, or wearable computing devices performing the particular actions.

Sensor devices 110 may include devices having one or more sensors that are configured to gather information about the user of ear-wearable device(s) 102 (e.g., user 105). In some examples, one or more of sensor devices 110 includes a body-worn device, such as a smartwatch, smart glasses, an implantable medical device, a Holter monitor, and so on. Example types of sensors may include electrocardiogram (EKG) sensors, photoplethysmogram sensors, heart rate sensors, body temperature sensors, inertial measurement units (IMUs), accelerometers, gyroscopes, electroencephalogram (EEG) sensors, magnetometers, image sensors, cameras, respiration sensors, pulse oximetry sensors, blood pressure sensors, eye movement sensors, eye-tracking sensors, microphones, pressure sensors, and so on.

Sensors of ear-wearable device(s) 102 and/or sensor devices 110 may generate signals that may be used to monitor user 105 for signs of various medical conditions. For example, the sensors may generate signals that may be used to monitor user 105 for signs that user 105 has fallen. In other examples, the sensors may generate signals that may be used to monitor the heart rate of user 105, generate an electrocardiogram of user 105, measure a respiration rate of user 105, measure a blood pressure of user 105, and measure the blood glucose of user 105. Furthermore, in some examples, the sensors may sense tremors that may be associated with epilepsy, Parkinson's disease, or other conditions. In some examples, one or more of the sensors may measure snoring or signals indicative of the quality of sleep of user 105.

Ear-wearable device(s) 102 may be configured to communicate with each other and sensor devices 110. Furthermore, at least one of ear-wearable device(s) 102 is configured to communicate with at least one of accessory devices 104. For example, ear-wearable device(s) 102, accessory devices 104, and sensor devices 110 may communicate wirelessly using wireless communication technology or a wire-based communication technology. Example types of wireless communication technology include Near-Field Magnetic Induction (NFMI) technology, a 900 MHz technology, a BLUETOOTH™ technology, a WI-FI™ technology, audible sound signals, ultrasonic communication technology, infrared communication technology, or another type of communication that does not rely on wires to transmit signals between devices. In some examples, ear-wearable device(s) 102, accessory devices 104, and sensor devices 110 may use a 2.4 GHz frequency band for wireless communication. In some examples, sensor devices 110 communicate with ear-wearable device(s) 102 and not with any other devices, such as accessory devices 104. In other examples, one or more of sensor devices 110 may communicate with one or more of accessory devices 104. In some examples, one or more of ear-wearable device(s) 102 may communicate with one or more of accessory devices 104 via wired communication links (e.g., via a cable, a direct electrical contact communication systems, etc.), wireless communication links (e.g., inductive communication links, audible sound communication links, ultrasonic communication links, infrared communication links, etc.), and other types of wired or non-wireless communication techniques.

Furthermore, in some examples, one or more of accessory devices 104 are configured to communicate with other. In some examples, two or more of accessory devices 104 communicate with each other via a communication network, such as network 106. As described elsewhere in this disclosure, network 106 may include a local area network, a wide area network, the Internet, or another type of communication network. In some examples, two or more of accessory devices 104 communicate directly with one another. For example, two or more of accessory devices 104 may communicate using NFMI technology, a BLUETOOTH™ technology, a ZIGBEE™ technology, audible sound communication, ultrasonic communication, or another type of wireless communication technology. In some examples, two or more of accessory devices 104 communicate directly with each other via wired communication links.

In the example of FIG. 1, sensor devices 110 may communicate with one or more of ear-wearable device(s) 102. Furthermore, in some examples, two or more of sensor devices 110 may communicate directly with each other without the involvement of ear-wearable device(s) 102. Although not shown in the example of FIG. 1, one or more of sensor devices 110 may communicate with one or more of accessory devices 104 without the involvement of any of ear-wearable device(s) 102.

It is often the case that user 105 or a third party is interested in maintaining or restoring the health of user 105. For example, if user 105 is healthy and without a chronic disease state, user 105 may be interested in viewing and analyzing vital signs or additional relevant body-sensor data. However, in the past, this required visits to clinics or hospitals where vitals and additional health-state measurements could be made. Improvements in technology allow for wearable sensors to acquire this data, but often require many independent, or invasive, or inconvenient sensors be applied to the wearers body. In some instances, these sensors limit mobility and are cumbersome.

In examples where user 105 has a chronic disease state or a family history of being at risk for a health condition, user 105 may benefit from wearing body sensors. If user 105 were able to provide their relevant body sensor data to a health monitoring service, acute medical emergencies might be averted by noticing trends prior to requiring emergency intervention. Not having the ability to monitor user 105 in this way may cause unnecessary hospital and emergency room admissions and may precipitate in medical and financial emergencies for user 105. Furthermore, even if a medical emergency is avoided, the healthcare system might instead require user 105 to submit to periodic clinical visits, e.g., to measure vital signs of user 105. However, as above, current options of remotely measuring user 105 with existing body-sensors may be cumbersome and inconvenient for user 105 and may be significantly less accurate when positioned on a more convenient location of the body, such as a wristwatch.

Further problems may exist because sensor devices 110 and ear-wearable device(s) 102 may have limited wireless transmission ranges (e.g., less than 10, 30, 50 feet). For example, sensor devices 110 may have wireless transmission ranges that do not significantly exceed ranges necessary to wirelessly communicate with ear-wearable device(s) 102 (or other sensor devices 110 that are able to communicate with ear-wearable devices). The limited wireless transmission ranges may be attributable to the small sizes of such devices, which may result in small battery capacity, attenuation due to the body of user 105, and other factors. Additionally, conserving battery power may be desirable in order to maintain the operations of such devices. Furthermore, due to the small size and limited battery power of ear-wearable device(s) 102 and sensor devices 110, the ability of ear-wearable device(s) 102 and sensor devices 110 to perform complex computations may be limited.

In some examples of this disclosure, accessory devices 104 include a mobile phone that acts as a support node for ear-wearable device(s) 102. A support node may be a device that provides communication and/or computational support to ear-wearable device(s) 102 and/or sensors 110. That is, the mobile phone may perform certain communication and/or computation functionality on behalf of ear-wearable device 102 and/or sensor devices 110. For instance, an application running on the mobile phone may perform support node functions for ear-wearable device(s) 102. In some examples, the mobile phone may communicate with ear-wearable device(s) 102 using BLUETOOTH™ Low Energy (BLE), audible sound communication, ultrasonic communication, infrared communication, WI-FI®, or another wireless communication technology. Offloading long-distance communication and/or computation to a mobile phone of user 105 may enable better communication and may reduce demands on power supplies of ear-wearable device(s) 102.

However, in some circumstances, the use of a mobile phone of user 105 as a support node may not be appropriate or sufficient for the needs of user 105. For example, ear-wearable devices, such as hearing assistance devices, are frequently used by the elderly, who may have reduced dexterity and limited familiarity with the use of smartphones. Moreover, many users do not typically carry their mobile phones around with them while at home, which may result in the mobile phones being out of wireless communication range of ear-wearable device(s) 102 and/or sensor devices 110. Mobile phones also require frequent charging, which might not be part of the typical routine of user 105. User 105 may also be wary of incurring charges for use data on their mobile phone. As a result, user 105 may intentionally or unintentionally power off the mobile phone of user 105. These factors may result in an unacceptably high probability that the mobile phone of user 105 is unavailable for use as a support node. Additionally, using a mobile phone as a support node for ear-wearable device(s) 102 and/or sensor devices 110 may require user 105 to purchase the mobile phone and remember to carry around the mobile phone. This may impose additional financial and mental burdens on user 105 or caregivers of user 105.

Hence, in accordance with one or more techniques of this disclosure, health monitoring system 100 includes a set of one or more accessory devices 104, which may act as a network of support nodes for ear-wearable device(s) 102. In some examples, the set of accessory devices 104 includes a mobile phone of user 105. In other examples, the set of accessory devices 104 does not include any mobile phone of user 105. By providing a broad list of types of devices that may be used as support nodes for ear-wearable device(s) 102, especially when the devices acting as support nodes are devices that user 105 would typically use with ear-wearable device(s) 102, it may be more likely that there will be one or more support nodes that fit the lifestyle of user 105.

As noted above, one or more of accessory devices 104 may be specifically-designed for use as accessories to ear-wearable device(s) 102. For example, accessory devices 104 may include charging devices, hearing aid accessories, media streamer devices, wireless relay devices, and other devices designed specifically for use as accessories to ear-wearable device(s) 102. Devices that are specifically-designed for use as accessories to ear-wearable device(s) 102 may have certain advantages over general-purpose devices as support nodes for ear-wearable device(s) 102.

For example, accessory devices 104 may include a charging device adapted to recharge power sources of ear-wearable device(s) 102. In this example, because user 105 may need to use the charging device to recharge ear-wearable device(s) 102, user 105 is likely to bring ear-wearable device(s) 102 within communication range of the charging device on a regular basis, thereby enabling ear-wearable device(s) 102 to offload data to the charging device for processing by at least one of the charging device, one or more other accessory devices 104, or computing devices 108.

In a similar example, accessory devices 104 may include a media streamer device. The media streamer device is configured to receive media data from a source device and wirelessly stream the media data to ear-wearable device(s) 102. For example, the media streamer device may have a cable that plugs into an audio output jack of the source device. In other examples, the media streamer device may have a wireless communication link, such as a BLUETOOTH™ communication link, with the source device. Example source devices may include a television, home or vehicle audio system, landline telephone, mobile phone, computer, smartwatch, wearable device, medical device, video game system, and so on. The media data may include audio data that ear-wearable device(s) 102 may play back to user 105. In this way, user 105 may have better access to higher-quality sound than user 105 would otherwise have if microphones of ear-wearable device(s) 102 were to detect sound generated directly by speakers of the source devices. Because user 105 may need to bring ear-wearable device(s) 102 within communication range of the media streamer device in order to access media data from the source device, user 105 is likely to bring ear-wearable device(s) 102 within communication range of the media streamer device on a regular basis, thereby enabling ear-wearable device(s) 102 to offload data to the media streamer device for processing by at least one of the media streamer device, one or more other accessory devices 104, or computing devices 108.

In another example, accessory devices 104 include a remote-control device configured to wirelessly control ear-wearable device(s) 102. For example, the remote-control device may have one or more buttons that enable user 105 to change the volume level of ear-wearable device(s) 102, one or more buttons to change audio profiles of ear-wearable device(s) 102, one or more buttons to toggle noise reduction, one or more buttons to turn ear-wearable device(s) 102 on and off, and/or buttons that control other aspects of ear-wearable device(s) 102. Because user 105 is likely to have a remote-control device close-by, ear-wearable device(s) 102 may be able to offload data to the remote-control device on a regular basis. Similar considerations apply with respect to remote microphone devices. A remote microphone device includes a microphone that may be placed close to a person to whom user 105 wants to listen. The remote microphone may transmit an audio signal to ear-wearable device(s) 102.

In some examples, two or more of accessory devices 104 may communicate with each other. In some such examples, two or more of accessory devices 104 may communicate directly with each other without the use of intermediate network devices. For instance, one of accessory devices 104 may receive a wireless transmission of data from another one of accessory devices 104.

Accessory devices 104 may communicate with each other for various purposes. For instance, in one example, a first accessory device may receive first data from ear-wearable device(s) 102. In this example, the first accessory device may send second data based on the first data to a second accessory device. The second accessory device may then process the second data. In this example, the second data may comprise a copy of the first data or the first device may perform intermediate processing on the first data to generate the second data. In this example, the first accessory device may send the second data to the second accessory device because the second accessory device may have greater power resources. For instance, the second accessory device may be connected to an electrical power grid while the first accessory device may be battery powered. Similarly, the first accessory device may send the second data to the second accessory device because the second accessory device has more capable processors than the first accessory device. In some examples, accessory devices 104 may forward data received from ear-wearable device(s) 102 (or data generated based on the data received from ear-wearable device(s) 102) to one or more of computing devices 108.

Accessory devices 104 and/or computing devices 108 may perform various types of actions using data received from ear-wearable device(s) 102 and/or sensor devices 110. For example, monitoring nodes (e.g., accessory devices 104 and/or computing devices 108) may generate wellness data based on the data received from ear-wearable device(s) 102 and/or sensor devices 110. The term wellness data may apply to various types of information that relate to the physical and/or mental wellness of user 105. For example, the wellness data may include achieved levels of one or more wellness measures, statistical data regarding user 105, and/or other types of information about user 105.

In some examples, as part of generating the wellness data, the monitoring nodes may identify negative trends or anomalies indicating a detrimental health-condition or trend in user 105. The monitoring nodes may store data for use in data trending, even if such data does not indicate an immediate threat to the health of user 105. Instead, data analysis and processing algorithms performed by the monitoring nodes may look for departures from either acceptable limits, or negative trends in health-related body-sensor data which warrant review by a qualified healthcare provide/monitoring service.

In examples in which accessory devices 104 send data to monitoring nodes (e.g., which may also be referred to as health monitoring endpoints) of health monitoring system 100, the monitoring nodes may use automated routines that seek to identify actionable medical conditions. In some examples, people may use the monitoring nodes to manually review the data. Furthermore, in some examples, health monitoring system 100 may use a combination of automated routines and humans to identify actionable medical conditions. Actionable medical conditions include medical conditions of user 105 upon which user 105 or another person may act. If a monitoring node identifies an actionable medical condition, one or more monitoring nodes of health monitoring system 100 may perform an action. For example, a monitoring node of health monitoring system 100 may communicate with user 105, dispatch emergency services, or alert other healthcare providers to take other actions at a later date (such as titrating prescription drug dosages with the intent of improving the patients/wearers health). Such actions by healthcare providers may be eligible for insurance reimbursement on an event-by-event basis or for reimbursement through any subscription/monitoring fees associated with the health monitoring service.

In some examples in which computing devices 108 select actions, computing devices 108 may use one or more of accessory devices 104 to perform the selected actions. For instance, in one example, computing device 108A may select an action that includes providing a notification to user 105. In this example, computing device 108A may send data to one or more of accessory devices 104 instructing the accessory devices 104 to cause ear-wearable device(s) 102 to provide the notification. The notification may comprise audible stimuli, tactile stimuli, haptic stimuli, electrical stimuli, or other types of stimuli. One or more haptic engines included in ear-wearable device(s) 102 may generate the tactile or haptic stimuli.

In some examples in which a plurality of accessory devices 104 are configured for use as accessories to ear-wearable device(s) 102, computing devices 108 may attempt to send actionable data to each of accessory devices 104 or one of accessory devices 104 may attempt to send actionable data generated or obtained by the accessory device to each other one of accessory devices 104. Thus, when ear-wearable device(s) 102 establishes a communication link with any of accessory devices 104, any of accessory devices 104 may interact with ear-wearable device(s) 102 to perform actions associated with the actionable data.

Various actions may be selected (e.g., by monitoring nodes such as accessory devices 104 or computing devices 108) for different health conditions. For example, if user 105 has seizures, selected actions may include titration of anti-seizure drugs. In another example where user 105 has seizures, the selected actions may include providing an audible warning of an impending seizure, which may allow user 105 to prepare for the seizure (e.g., by pulling over their car or stopping machinery) or summoning assistance. In examples where user 105 snores or has poor sleep quality, the selected actions may include providing notifications (e.g., audible, tactile, haptic, electrical, and/or other types of stimuli) to assist in minimizing snoring. In examples where user 105 is diabetic, the selected actions may include providing an audible notification prompting user 105 to boost or lower their blood glucose.

Furthermore, in some examples, user 105 suffers from Alzheimer's disease or dementia and is prone to wandering away from home or other safe location. Accordingly, the selected actions may include notifying one or more caregivers that user 105 has potentially gotten lost. In this example, one or more monitoring nodes of health monitoring system 100 may determine that user 105 has wandered away if ear-wearable device(s) 102 are not within wireless communication range of any of accessory devices 104. That is, accessory devices 104 may determine that ear-wearable device(s) 102 are no longer within wireless communication range of any of accessory devices 104. In response to determining that ear-wearable device(s) 102 are no longer within wireless communication range of any of the accessory devices, accessory devices 104 may trigger a computing device (e.g., one of computing device 108) to generate an alert to a party other than user 105 of ear-wearable device(s) 102.

In some examples, the actions selected by monitoring nodes of health monitoring system 100 may include targeted notifications that prompt user 105 to maintain a healthy lifestyle. For instance, such targeted notifications may include medication reminders, nutrition reminders, reminders to exercise, and so on. In some examples, the targeted notifications may include audible messages played back by ear-wearable device(s) 102. In other examples, the targeted notifications may include email messages, text messages, voicemail messages, or other types of messages. In some examples, targeted notifications may be played back through audio gateway devices, such as a smart speaker device (e.g., an ECHO™ device from Amazon.com, Inc. or a GOOGLE HOME™ device from Google LLC.).

In some examples, user 105 may initiate monitoring of one or more aspects of the health of user 105. For example, user 105 may initiate monitoring if user 105 feels that an acute health episode is occurring or impending. Examples of acute health episodes may include anomalous heart rhythms, low blood pressure, hypo- or hyper-glycemia, falls, symptoms of impending seizures, and so on. In examples where user 105 initiates monitoring, ear-wearable device(s) 102 may expend greater energy than ear-wearable device(s) 102 typically would expend in order to establish a communication link with one of accessory devices 104. For instance, ear-wearable device(s) 102 may transmit data at a maximum power level, even though doing so may quickly deplete the power source of ear-wearable device(s) 102. Likewise, battery-powered accessory devices may wirelessly transmit data at high power levels if doing so is required to communicate with one or more other ones of accessory devices 104 or computing devices 108.

In some examples, accessory devices 104 may help people locate user 105. For example, there may be multiple accessory devices 104 configured for use with ear-wearable device(s) 102 and the communication links between accessory devices 104 and ear-wearable device(s) 102 are wireless communication links. Furthermore, accessory devices 104 may be associated with fixed locations within a building. For instance, a charging device may be stored in the bedroom of user 105, a first media streamer device may be connected to a television in a living room and a second media streamer device may be connected to a television in a kitchen. Monitoring nodes (e.g., accessory devices 104 or computing devices 108) may estimate, based on wireless signals emitted by ear-wearable device(s) 102 and detected by one or more of accessory devices 104, a location of ear-wearable device(s) 102. For instance, in some examples, monitoring nodes may triangulate the location of ear-wearable device(s) 102 based on the wireless signals. For instance, the monitoring nodes may triangulate the locations of ear-wearable device(s) 102 based on signal strengths of the wireless signals. Additionally or alternatively, where one or more of the monitoring nodes has multiple antennas, transmitters or receivers, the monitoring nodes may triangulate the locations of ear-wearable device(s) 102 based on the angle of arrival, and/or angle of departure of the wireless signals. Thus, in some examples where an accessory device has multiple antennas, the accessory device may determine the location of ear-wearable device(s) 102 without involvement of other accessory devices 104. Certain types of accessory devices, such as charging devices and media streamer devices, are especially likely to remain at fixed positions, which may enhance their ability to estimate the location of ear-wearable device(s) 102. This may be advantageous relative to other types of devices, such as mobile phones, that are by nature more mobile.

In some examples, monitoring nodes may send navigation information to a computing device. The navigation information may indicate the estimated location of the ear-wearable device. The computing device in this example may be a mobile device of a caregiver, family member, first responder, emergency medical technician (EMT), or another individual who may need to find user 105 quickly (e.g., in the event of an acute health episode or user 105 wandering away). Thus, in one such example, health monitoring system 100 includes a plurality of accessory devices 104 and the communication links between accessory devices 104 and ear-wearable device(s) 102 are wireless communication links. In this example, accessory devices 104 may estimate, based on wireless signals emitted by ear-wearable device(s) 102 and detected by accessory devices 104, a location of ear-wearable device(s) 102. In this example, accessory devices 104 may send navigation information to a computing device (e.g., one of computing devices 108), where the navigation information indicates the estimated location of the ear-wearable device. In some examples, monitoring nodes may send notifications to one or more third parties if the estimated location of user 105 is outside a predefined area. Thus, ear-wearable devices 102 may serve as a virtual ankle bracelet for nursing homes, electronic fence applications, and so on.

In some examples, ear-wearable device(s) 102 and/or accessory devices 104 may communicate with one or more medical devices used by user 105. Example medical devices may include implanted medical devices, body-worn medical devices, home medical devices, and other types of medical devices. In some examples, ear-wearable device(s) 102 or accessory devices 104 may transmit actionable data generated by monitoring nodes of health monitoring system 100 to one or more medical devices used by user 105. In one example, the actionable data may cause an implanted drug pump to administer a medication. In some examples, the actionable data may cause ear-wearable device(s) 102 to interact with other body-worn or implantable medical devices to perform electrical or medical stimulation. In some examples, example, the actionable data may change configuration settings of a medical device.

In some examples, one or more medical devices used by user 105 may transmit information to health monitoring system 100 e.g., by way of ear-worn devices 102. Monitoring nodes of health monitoring system 100 (e.g., accessory devices 104, computing devices 108, etc.) may use such data as part of performing health monitoring activities. For example, a medical device may transmit information indicating a battery power level of the medical device. In this example, as part of performing health monitoring activity, a monitoring node may generate, based on the information transmitted by the medical device, actionable data that when received by ear-wearable device(s) 102 causes ear-wearable device(s) 102 to output an audible notification that the power level of the battery of the medical device is low. In another example, a defibrillator device implanted in user 105 may transmit information indicating that the defibrillator device will imminently begin defibrillation. In this example, a monitoring node may generate, based on the information transmitted by the defibrillator device, actionable data that when received by ear-wearable device(s) 102 cause ear-wearable device(s) 102 to output an audible warning of imminent defibrillation. In another example, the monitoring node may notify a third party of the imminent defibrillation. Health monitoring activities may include activities that monitor one or more health conditions of a user and generate output based on the health conditions of the user.

Privacy is a concern for many users. For instance, user 105 may feel uncomfortable having a large amount of personal data stored on the cloud. Moreover, the storage of such personal data on the cloud may present security and regulatory risks to a party, such as a manufacturer of ear-wearable device(s) 102 or a health monitoring service, that collects and stores the personal data. Hence, in accordance with the techniques of this disclosure, accessory devices 104 may process certain types of personal data locally, without transmitting the personal data to cloud-based processing nodes such as computing devices 108. In this way, health monitoring system 100 may avoid the transmission and/or storage of certain types of personal data by cloud-based computing devices.

As noted elsewhere in this disclosure, two or more accessory devices 104 may communicate with each other directly or indirectly. For example, accessory device 104A and accessory device 104N may communicate with each other. In certain examples where two or more accessory devices 104 may communicate with each other, one of accessory devices 104 may forward personal data or intermediate data to another one of accessory devices 104 for further processing. For example, accessory device 104A may be a portable charging case for ear-wearable device(s) 102 and accessory device 104N may be a media streamer device configured for use with ear-wearable device(s) 102. In this example, the portable charging case may receive personal data from one or more of ear-wearable device(s) 102. Because the media streamer device, unlike the portable charging case, may have access to power from an electrical grid, the portable charging case may forward the personal data to the media streamer device, which may then perform one or more health monitoring activities.

In some examples, accessory devices 104 may share information with each other that enable accessory devices 104 to determine which of accessory devices 104 should perform particular health monitoring activities. For instance, accessory device 104A may share information indicating that accessory device 104A has access to a grid power source and has a first type of processor. In this example, accessory device 104N may share information indicating that accessory device 104N has a second type of processor. Based on this shared information, each of accessory devices 104 may determine that accessory device 104A is current the best equipped to perform the health monitoring activities. Which one of accessory devices 104 performs the health monitoring activities may change as different accessory devices 104 are added or removed from a group of active accessory devices.

Monitoring nodes may use various types of computational techniques to perform monitoring activities. For example, a monitoring node may perform monitoring activities using business rules, artificial intelligence techniques (e.g., neural networks), and so on.

Figure 2:
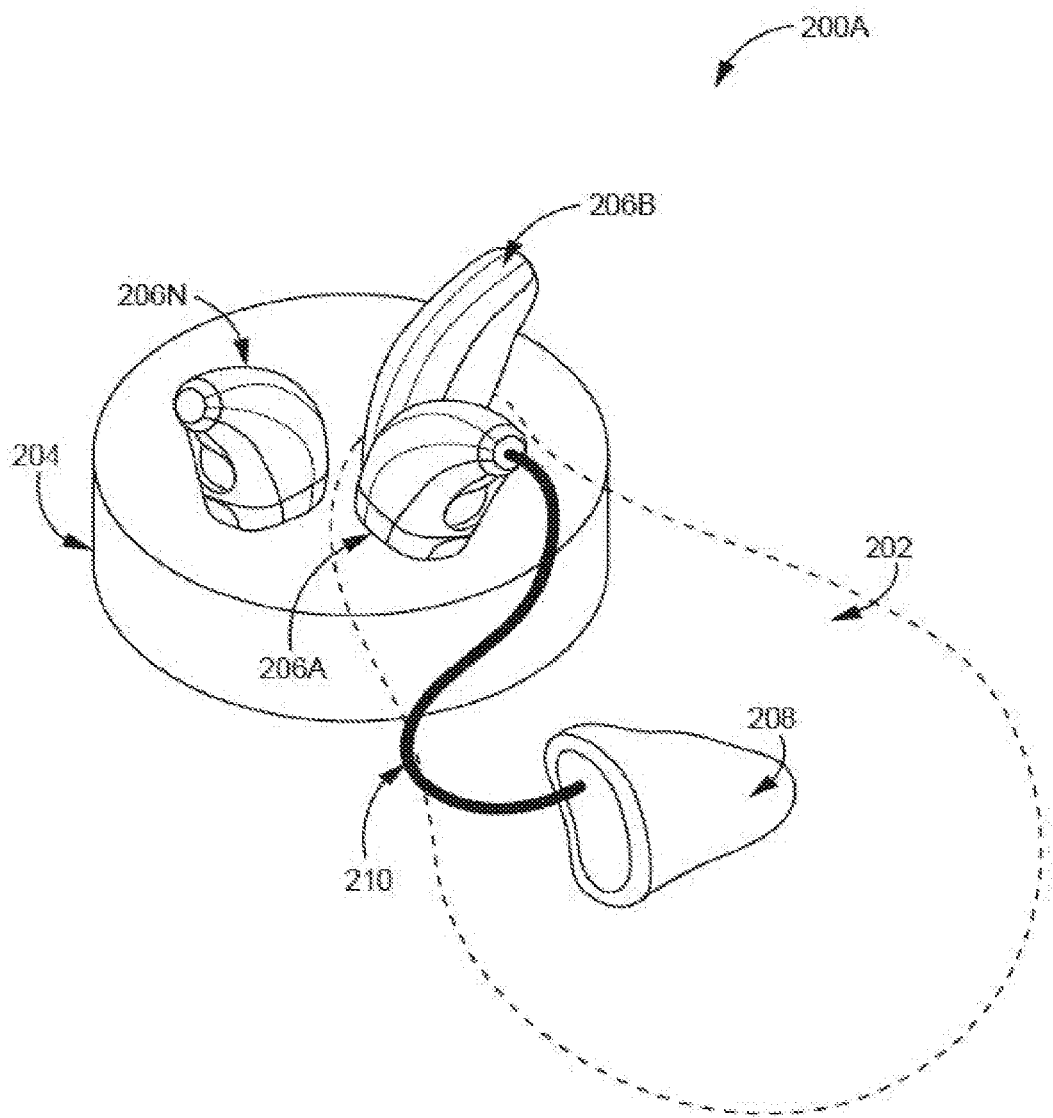
FIG. 2 is a conceptual diagram illustrating an example system, in accordance with one or more aspects of the present disclosure.

FIG. 2 is a conceptual diagram illustrating an example system, in accordance with one or more aspects of the present disclosure. FIG. 2 is described in the context of health monitoring system 100 of FIG. 1. For instance, FIG. 2 includes a hearing assistance device 202 and a portable case 204. HAD 202 may be one of ear-wearable device(s) 102. Portable case 204 may be one of accessory devices 104.

In the example of FIG. 2, HAD 202 includes a behind-ear portion 206A coupled to an in-ear portion 208 via a tether 210. Behind-ear portion 206A of HAD 202 is housed in a retention structure of portable case 204, for example, either to be subsequently detached from tether 210 for charging, or to be removed from portable case 204 via tether 210 to be worn by a user. In addition to storing (and in some instances charging) a power source of behind-ear portion 206A, portable case 204 also may charge one or more other behind-ear portions. For example, in FIG. 2, portable case 204 is also shown storing and/or charging behind ear portions 206B and 206N. In the example of FIG. 2, portable case 204 is configured in a carousel arrangement to facilitate quick and easy exchange of one behind-ear portion 206 for a different behind-ear portion 206. In other examples, portable case 204 may be configured in a linear or other such arrangement.

Figure 3:
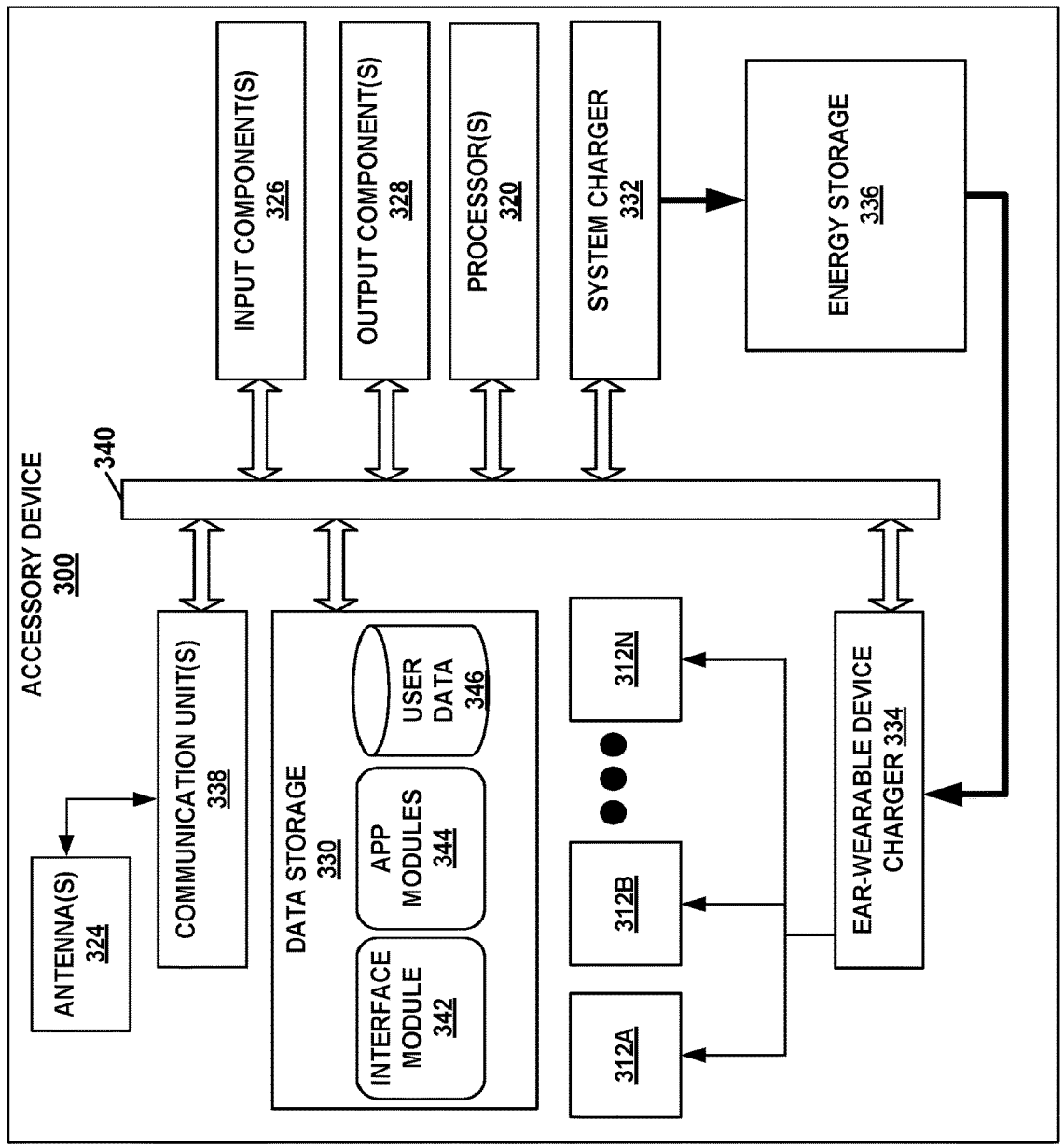
FIG. 3 is a block diagram illustrating an example portable case for storing and charging behind-ear portions of an example hearing assistance device, in accordance with one or more aspects of the present disclosure.

FIG. 3 is a block diagram illustrating an example accessory device 300 in accordance with one or more aspects of this disclosure. Accessory device 300 may be various types of devices. For example, accessory device 300 may be a media streamer device. In another example, accessory device 300 may be a portable case for storing and charging ear-wearable device(s) 102. Accessory device 300 is an example of accessory devices 104 of FIG. 1 and/or portable case 204 204 of FIG. 2. Accessory device 300 may include additional or fewer components than those shown in FIG. 3.

In the example of FIG. 3, accessory device 300 includes one or more input components 326, one or more output components 328, one or more processors 320, data storage device 330, one or more transceivers 322, one or more antennas 324, a system charger 332, an energy storage device 336, one or more communication units 338, and communication bus 340. Data storage device 330 may include interface module 442, various application modules 444, and user data 446. In some examples in which accessory device 300 comprises a charging case, accessory device 300 may include retention structures 312A-312N, and ear-wearable device charger 334. In other examples, accessory device 300 does not include retention structures 312A-312N and ear-wearable device charger 334. For instance, in examples where accessory device 300 is a remote microphone device, accessory device 300 may include one or more microphones.

Communication bus 340 interconnects at least some of the components 322, 324, 326, 328, 320, 330, 332, 334, and 338 for inter-component communications. That is, each of components 322, 324, 326, 328, 320, 330, 332, 334, and 338 may be configured to communicate and exchange data via a connection to communication bus 340. In some examples, communication bus 340 is a wired or wireless bus. Communication bus may include a system bus, a network connection, an inter-process communication data structure, or any other method for communicating data.

Input components 326 are configured to receive various types of input, including tactile input, audible input, image or video input, sensory input, and other forms of input. Non-limiting examples of input components 326 include a presence-sensitive input device or touch screen, a button, a switch, a key, a microphone, a camera, or any other type of device for detecting input from a human or machine. Other non-limiting examples of input components 326 include one or more sensor components, such as a proximity sensor, a global positioning system (GPS) receiver or other type of location sensor, an accelerometer, an inertial measurement unit (IMU), a temperature sensor, a barometer, a gyro, an ambient light sensor, a proximity sensor, a hydrometer sensor, a heart rate sensor, a magnetometer, a glucose sensor, an olfactory sensor, a compass, a magnetometer, an antennae for wireless communication and location sensing, a step counter, to name a few other non-limiting examples.

Output components 328 are configured to generate various types of output, including tactile output, audible output, visual output (e.g., graphical or video), and other forms of output. Non-limiting examples of output components 328 include a sound card, a video card, a speaker, a display, a projector, a vibration device, a light, a light emitting diode (LED), or any other type of device for generating output to a human or machine.

One or more communication units 338 enable accessory device 300 to communicate with external devices (e.g., computing devices 108 and/or ear-wearable device(s) 102) via one or more wired and/or wireless connections. Communication units 338 transmit and receive signals being transmitted across network 106 and convert the network signals into readable data used by any of components 322, 324, 326, 328, 320, 330, 332, 334, and 338. One or more antennas 324 are coupled to communication units 338 and are configured to generate and receive the signals that are broadcast through the air (e.g., via network 106).

Examples of communication units 338 include various types of receivers, transmitters, transceivers, Bluetooth radios, short wave radios, cellular data radios, wireless network radios, universal serial bus (USB) controllers, proprietary bus controllers, network interface cards, optical transceivers, radio frequency transceivers, or any other type of device that can send and/or receive information over a network. In cases where communication units 338 include a wireless transceiver, communication units 338 may be capable of operating in different radio frequency (RF) bands (e.g., to enable regulatory compliance with a geographic location at which accessory device 300 is being used). For example, a wireless transceiver of communication units 338 may operate in the 900 MHz or 2.4 GHz RF bands. A wireless transceiver of communication units 338 may be a near-field magnetic induction (NFMI) transceiver, and RF transceiver, an Infrared transceiver, ultra-sonic transceiver, or other type of transceiver.

In some examples, communication units 338 are configured as wireless gateways that manage information exchanged between accessory device 300, and ear-wearable device(s) 102, computing devices 108, and other devices. As a gateway, communication units 338 may implement one or more standards-based network communication protocols, such as Bluetooth®, Wi-Fi®, GSM, LTE, WiMax®, 802.1X, Zigbee®, LoRa® and the like as well as non-standards-based wireless protocols (e.g., proprietary communication protocols). Communication units 338 may allow ear-wearable device(s) 102 to communicate, using a preferred communication protocol implementing intra and inter body communication (e.g., an intra or inter body network protocol), and convert the body communications to a standards-based protocol for sharing the information with other computing devices, such as computing devices 108. Whether using a body network protocol, intra or inter body network protocol, body area network protocol, body sensor network protocol, medical body area network protocol, or some other intra or inter body network protocol, communication units 338 enable ear-wearable device(s) 102 to communicate with other devices that are embedded inside the body, implanted in the body, surface-mounted on the body, or being carried near a person's body (e.g., while being worn, carried in or part of clothing, carried by hand, or carried in a bag or luggage).

Communication units 338 enable ear-wearable device(s) 102 to communicate with other computing devices, such as computing devices 108 even though ear-wearable device(s) 102 may only communicate using a non-standard communication protocol. Communication units 338 may convert a standards-based communication from one of computing devices 108 to a non-standards-based protocol associated with ear-wearable device(s) 102, and vice versa.

Energy storage 336 represents a battery (e.g., a well battery), a capacitor, or other type of electrical energy source or storage device that is configured to power components of accessory device 300. Energy storage 336 may be coupled to system charger 332. System charger 332 is responsible for performing power management and charging of energy storage 336. System charger 332 may comprise a buck converter, boost converter, flyback converter, or any other type of AC/DC or DC/DC power conversion circuitry adapted to convert power (such as power from an electrical grid) to a form of electrical power suitable for charging energy storage 336. In some examples, system charger 332 includes a charging antenna (e.g., NFMI, RF, or other type of charging antenna) for wirelessly recharging energy storage 336. In some examples, system charger 332 includes photo-voltaic cells, which may protrude through a housing of accessory device 300 or otherwise be coupled to accessory device 300 for recharging energy storage 336. In some examples, system charger 332 relies on a wired connection to a power source for charging energy storage 336.

In examples in which accessory device 300 includes a charging case, accessory device 300 may include retention structures 312A-312N (collectively referred to as "retention structures 312") configured to receive portions of ear-wearable device(s) 102 (e.g., behind-ear portions of ear-wearable device(s) 102) for charging. Retention structures 312 may include mechanical and/or magnetic attachment features that, after manipulation by a user, automatically attach or detach portions of ear-wearable device(s) 102. Each of retention structures 312 is electrically coupled to energy storage 336 and ear-wearable device charger 334. When ear-wearable device charger 334 enables retention structures 312 for charging, electrical current passes from energy storage 336 to retention structures 312 (e.g., via some charging circuitry).

Retention structures 312 may provide a magnetically coupled electrical connection between a power source of an ear-wearable device (e.g., a behind-ear portion of an ear-wearable device) and ear-wearable device charger 334. Retention structures 312 may include one or more mechanical stops to ensure correct seating and/or to prevent removal of the coupled portions of the ear-wearable devices when charging. Retention structures 312 may include respective retention structures that enable easy insertion of depleted portions of ear-wearable device(s) 102 and locks the depleted portions of ear-wearable device(s) 102 in place. The mechanical and/or magnetic attachment features of retention structures 312 may enable easy insertion of the portions of ear-wearable device(s) 102 and may require a sufficient amount of force to overcome the mechanical and/or magnetic attachment features during removal.

Ear-wearable device charger 334 includes charging circuitry that is electrically coupled to each of retention structures 312 and is responsible for enabling or disabling each of retention structures 312 for charging power sources of ear-wearable device(s) 102. Ear-wearable device charger 334 may further exchange data between ear-wearable device 102 (e.g., behind-ear portions of ear-wearable device(s) 102) located in retention structures 312 and other components of accessory device 300. Ear-wearable device charger 334 may cause the magnetic connection between the power source of an ear-wearable device and ear-wearable device charger 334 to be stronger when charging the power source and weaker or reversed after the power source is charged (e.g., using electro-permanent magnets activated and deactivated by circuitry). Such electro-permanent magnets may be configured by a pulse of energy supplied by energy storage 336 and ear-wearable device charger 334. Such energy may be supplied from ear-wearable device charger 334 through direct connection or magnetic induction to the electro-permanent magnet. It should be understood that one or more electro-permanent magnets may be included in either, or both, a behind-ear portion of an example hearing assistance device and accessory device 300. Furthermore, any combination of any of the following: electro-permanent magnets(s), permanent magnet(s), and ferrous material, may be used by at least one of a behind-ear portion of an example ear-wearable device and accessory device 300 to achieve a strong bond between accessory device 300 and the charging behind-ear portion.

One or more processors 320 execute operations that implement functionality of accessory device 300. For example, processors 320 may perform health monitoring activities. Processors 320 may be implemented as fixed-function processing circuits, programmable processing circuits, or a combination of fixed-function and programmable processing circuits. Examples of processors 320 may include digital signal processors, general purpose processors, application processors, embedded processors, graphic processing units (GPUs), digital signal processors (DSPs), application specific integrated circuits (ASICs), field programmable gate arrays (FPGAs), display controllers, auxiliary processors, sensor hubs, input controllers, output controllers, microcontrollers, and any other equivalent integrated or discrete hardware or circuitry configure to function as a processor, a processing unit, or a processing device.

Data storage device 330 of accessory device 300 may comprise one or more fixed and/or removable data storage units configured to store information for subsequent processing by processors 320 during operations of accessory device 300. In other words, data storage device 330 may retain data accessed by modules 342 and 344 as well as other components of accessory device 300 during operation. Data storage device 330 may, in some examples, include a non-transitory computer-readable storage medium that stores instructions, program information, or other data associated modules 342 and 344. Processors 320 may retrieve the instructions stored by data storage device 330 and execute the instructions to perform operations described herein.

Data storage device 330 may include a combination of one or more types of volatile or non-volatile memories. In some cases, data storage device 330 includes a temporary or volatile memory (e.g., random access memories (RAM), dynamic random-access memories (DRAM), static random-access memories (SRAM), and other forms of volatile memories known in the art). In such a case, data storage device 330 is not used for long-term data storage and as such, any data stored by storage device 330 is not retained when power to data storage device 330 is lost. Data storage device 330 in some cases is configured for long-term storage of information and includes non-volatile memory space that retains information even after data storage device 330 loses power. Examples of non-volatile memories include magnetic hard discs, optical discs, flash memories, USB disks, or forms of electrically programmable memories (EPROM) or electrically erasable and programmable (EEPROM) memories.

Interface module 342 and application modules 344 represent any combination of hardware, software, and firmware units that are operable by processors 320 to perform operations of accessory device 300. For example, processors 320 may retrieve and execute instructions stored by data storage device 330 that cause processors 320 to perform the operations of interface module 342 and application modules 344. By executing the instructions associated with interface module 342 and application modules 344, processors 320 may store or write information to data storage device 330.

Interface module 342 implements a user interface associated with accessory device 300, for example, by translating inputs detected by accessory device 300 to commands for performing operations or generating corresponding outputs. Interface module 342 receives information about inputs detected by input components 326 and in response, generates information for causing output components 328 to produce output. For example, interface module 342 may receive information from a microphone of input components 326, determine that a user is speaking a command to accessory device 300, and perform an operation in response.

Interface module 342 may detect two-dimensional and/or three-dimensional gestures as input from a user of accessory device 300. For instance, a sensor or IMU of input components 326 may detect a user's movement (e.g., moving a hand, an arm, a pen, a stylus, etc.) within a threshold distance of the sensor. Interface module 342 may determine a two or three-dimensional vector representation of the movement and correlate the vector representation to a gesture input (e.g., a hand-wave, a pinch, a clap, a pen stroke, etc.) that has multiple dimensions. Interface module 342 may receive information from an IMU and/or magnetometer of input components 326, determine that a user is performing a hand gesture with accessory device 300 in-hand, and perform an operation in response.

Interface module 342 may provide a graphical user interface, an audible user interface, a haptic interface, or a combination thereof. The user interface provided by interface module 342 may in some examples a battery gauge. The battery gauge may indicate battery levels of behind-ear portions 106 that are seated in retention structures 312. The battery gauge may indicate a battery levels of energy source 336. A user may interact with the battery gauge provided by interface module by providing verbal inputs (e.g., to a microphone of input components 326), touch inputs (e.g., to a touch screen of input components 326), or via haptic components (e.g., detected by an IMU of input components 326). For example, if a user shakes accessory device 300, the movement detected by movement sensors of input components 326 may indicate to interface module 342 that a user wishes to learn the charging status of behind-ear portions 106. In response to the shake input, interface module 342 may cause a speaker of output components 328 to generate audible output that "speaks" the battery level to the user. Other combinations of touch, voice, or haptic input and visual, audible, and haptic outputs are possible.

Application modules 344 include any application or software that accessory device 300 may execute to implement the functionality of accessory device 300 that is described in this disclosure. For example, application modules 344 may perform health monitoring activities, as described elsewhere in this disclosure. In some examples, application modules 344 may include machine-learning or artificial intelligence software (e.g., for performing the health monitoring activities described elsewhere in this disclosure), an Internet browser, a media player, a file system, a map or navigation program, or any other number of applications or features that accessory device 300 may include. Other examples of application modules 344 include programming software for using accessory device 300 as a programmer for ear-wearable device(s) 102, a personal assistant application, a messaging or personal communication application, an audio recording application, or other application.

In some cases, application modules 344 include an audio controller application. The audio controller application may interact with communication units 338 to scan for available wireless audio broadcasts within range of antennas 324 and cause interface module 342 to alert a user of potential audio sources (e.g., via audible, tactile, or visual feedback). The audio controller application may receive information obtained by interface module 342 (e.g., after input components 326 detect spoken or touch inputs from a user) that is interpreted by the audio controller application as an input to select a particular audio source or broadcast.

Application modules 344, in some examples, include a remote-control application. The remote-control application enables a user to provide inputs to accessory device 300 that alter settings of ear-wearable device(s) 102, or some other computing device, such as one of computing devices 108.

In some examples, such as examples in which accessory device 300 is a remote microphone device, application modules 344 may include a remote microphone application. The remote microphone application enables a user to position accessory device 300 near a desired audio source (e.g., another person, a speaker, etc.) and hear the audio being picked up by accessory device 300, in his or her ear as the audio is played back via one or more of ear-wearable device(s) 102. For instance, the remote microphone application may cause a microphone of input components 326 to start recording audio. In seemingly near real-time, the remote microphone application processes the recorded audio and sends the recorded audio via communication units 328 to ear-wearable device(s) 102, or some other external device.

Application modules 344 may include a personal assistant application or other artificial intelligence application that interacts with a user to perform various functions. For example, the assistant may help a user configure a hearing instrument for a particular environment, access the Internet to perform various tasks on behalf of the user, or perform other assistant functionality.

Artificial intelligence capability provided by application modules 344 could be distributed (with varying degrees of capability) amongst various components connected to network 105. For example, the artificial intelligence capability may execute in whole or part at accessory device 300, other ones of accessory devices 104, ear-wearable device(s) 102, other personal electronics in a body-area-network, and at computing devices 108 (e.g., in a cloud-based networked application environment).

With permission from a user, an artificial intelligence application may monitor conversations being detected by a microphone of input components 326 using voice recognition techniques (e.g., identifying a quantity of individual participants and their roles in the conversation), and when necessary perform targeted cloud-based searches on behalf of the user or near real-time translations. The artificial intelligence application may cause portable case to audibly, visually, or using haptic feedback, coach the user by causing output components 328 to output additional data, answers to questions, or cues when needed.

In some cases, the artificial intelligence application could be used to interpret speech in the context of a conversation and "regenerate" a much higher signal-to-noise ratio version of the received audio by performing word or speech synthesis. The artificial intelligence application may cause accessory device 300 to output (e.g., in a computer-generated voice synthesized by the artificial intelligence application that in some cases mimics the original source) the regenerated audio either via a speaker embedded in output components 328, or via one or more speakers of ear-wearable device(s) 102. The regenerated audio may in some cases be translated from one language to another, in some instances, even correcting for grammatical errors. Such a feature may significantly reduce or off-load the cognitive burden a user may otherwise experience listening to speech in a noisy environment. In other applications, the neural network may be employed to make automatic adjustments to ear-wearable device(s) 102 based on the acoustic environment that the wearer is in. These adjustments may be based on sound the microphone picks up from either accessory device 300, another one of accessory devices 104, or ear-wearable device(s) 102, themselves. Other adjustments may be more direct from voice commands from the user.

In some examples, the artificial intelligence application comprises a neural network. For example, the artificial intelligence application may include a neural network for sound processing, sound classification, object or image classification, health condition classification, action selection, and so on. In such an example, accessory device 300 may include (or be communicatively coupled to one located in ear-wearable device(s) 102) an ultrasonic transducer and sensor and/or one or more image sensors for determining ranges to objects and/or density of objects. As such, accessory device 300 may execute the artificial application to perform (e.g., body-worn) assistance and navigation for a seeing impaired user.

User data 346 includes any information stored by accessory device 300 on behalf of a user. User data 346 includes preferences or settings associated with accessory device 300 and ear-wearable device(s) 102. User data 346 may include calendar information, messages, alerts, warnings, alarms, e-mails, address book or contact information, music files, audio book files, or other audio files that a user of accessory device 300 may wish to access, e.g., via a media player application 344 executing at accessory device 300. User data 346 may be stored on removable media of data storage 330. A user may swap out the removable storage media for removable storage media that includes other music, audio books, etc. In some cases, user data 346 includes medical or financial records of the user, and other information that the user may want to have on hand at all times. For example, user data 346 may include an audio recording of a user's medical insurance record, medical records, and medical alerts. User data 346 may include a digital wallet with personal credit card information, cryptocurrency information, passwords, cryptographic keys, authentication keys, and other types of data.

Application modules 344 may use user data 346 to perform an operation. Application modules 244 may write or modify user data 346. For example, an assistant application may utilize user data 346 to complete a task (e.g., when a user commands the assistant to tell the user about his or her daily schedule).

Accessory device 300 and data storage 330 may ensure that user data 346 is encrypted, secure, and/or password protected to prevent malicious use. Such passwords or encryption keys may be authenticated via sensory information obtained from ear-wearable device(s) 102 or other external device. For example, a user may speak a password, the spoken audio may be picked up by a microphone of input components 326 or a microphone of ear-wearable device(s) 102. Using voice-recognition, face-recognition, or authentication techniques, accessory device 300 may validate the user (e.g., the user's voice, fingerprint, or facial image) or invalidate the user. In response to validating the password or key, accessory device 300 may unlock and grant access to user data 346. In response to invalidating the voice input, accessory device 300 may prevent access to user data 346. In other examples, passwords and keys could be authenticated via on-board biometry sensors of input components 326 (e.g., a fingerprint sensor, a temperature sensor, a camera or image sensor configured to perform facial recognition, or other sensor) or ear-wearable device(s) 102. In some examples, in response to ear-wearable device(s) 102 or portable case 104 authenticating a user (e.g., a wearer of ear-wearable device(s) 102), ear-wearable device(s) 102 and/or portable case 104 may act as a "universal password wallet/or key repository" that communicates via an encrypted/secure wireless connection with other wirelessly enabled devices that require user authentication before granting access to the other wirelessly enabled devices (e.g. computers, smart-phones, automobile automation/locks, home automation/locks, etc.)

Figure 4:
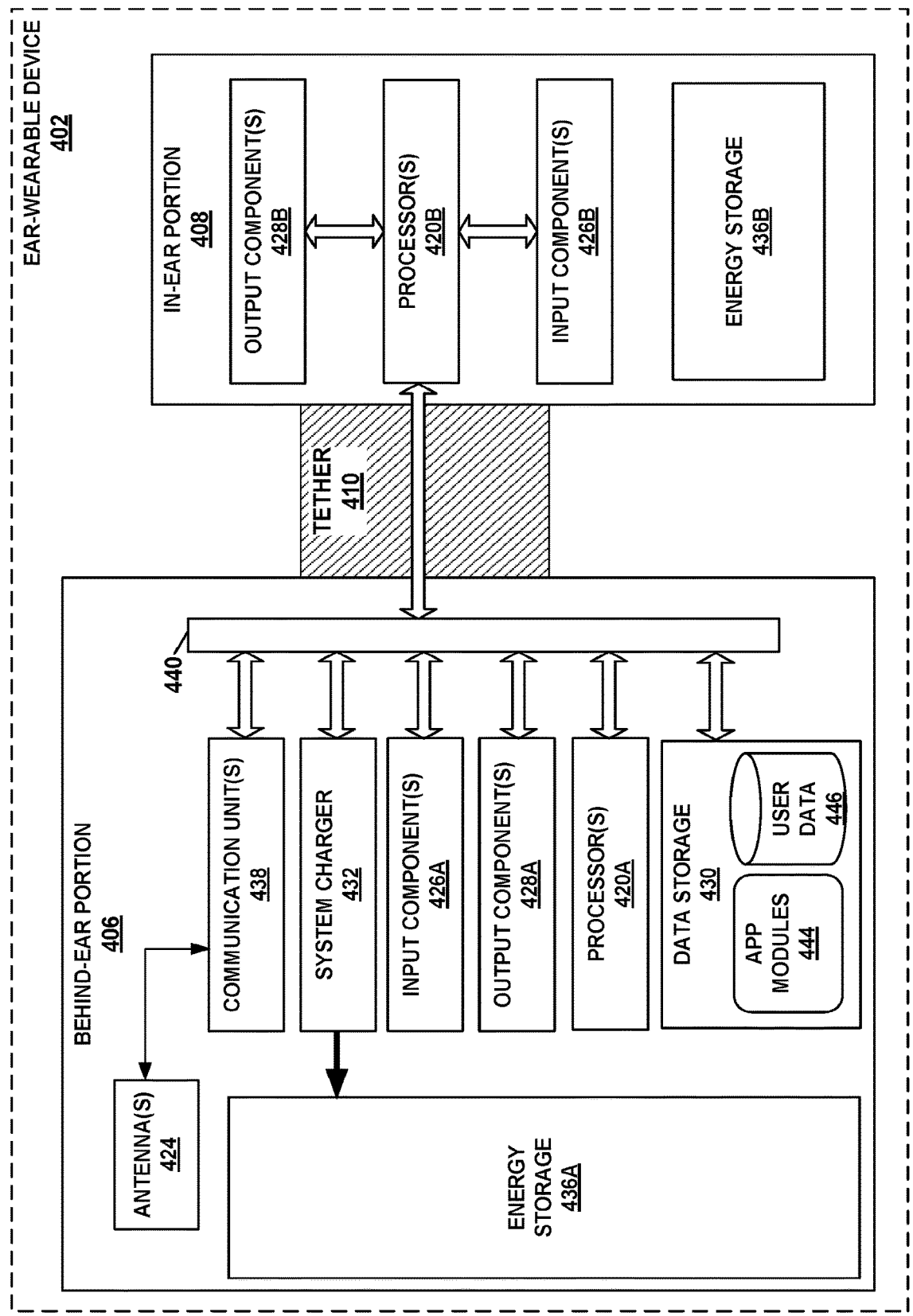
FIG. 4 is a block diagram illustrating an example hearing assistance device, in accordance with one or more aspects of the present disclosure.

FIG. 4 is a block diagram illustrating an example ear-wearable device 400, in accordance with one or more aspects of the present disclosure. As shown in the example of FIG. 4, ear-wearable device 402 includes behind-ear portion 406 operatively coupled to in-ear portion 408 via tether 410. Ear-wearable device 400 is an example of ear-wearable device(s) 102 of FIG. 1 and ear-wearable device 202 of FIG. 2. Ear-wearable device 400 is described in the context of FIG. 1 and FIG. 2. It should be understood that ear-wearable device 400 is only one example of a hearing assistance device according to the described techniques. Ear-wearable device 400 may include additional or fewer components than those shown in FIG. 4. For example, ear-wearable device 400 is presented as having a behind-ear portion and an in-ear portion. In other examples, ear-wearable device 400 may be a BTE, ITE, ITC, CIC, or IIC type ear-wearable device. In such examples, a tether may not be present and certain components shown in the example of FIG. 4 may be contained within a single shell.

Examples of each of the components of ear-wearable device 400 include the examples of each of the similarly-named components of accessory device 300 described above. For instance, processors 420A and 420B may be similar to examples of processors 320 described above and examples of input components 426A and 426B and output components 428A and 428B include the respective examples of input components 326 and output components 328 described above. In addition, processors 420A and 420B may include or access local memory of behind-ear portion 406 and in-ear portion 408, respectively, to perform the operations described herein.

Tether 410 operatively (e.g., electrically, physically, and communicatively) couples behind-ear portion 406 with in-ear portion 408. Tether 410 is an example of tethers 110 and 210 and uses a combination of one or more wired communication links to transfer information and electrical energy between portions 406 and 408. Tether 410 may be configured as a handle for a user to grip ear-wearable device 400.

In-ear portion 408 is a part of ear-wearable device 400 responsible for outputting sound for hearing. In-ear portion 408 includes core electro-acoustic features of ear-wearable device 400, including one or more processors 420B, such as one or more digital signal processors, one or more output components 428B, such as a speaker, and one or more input components 426B, such as a microphone. In-ear portion 408 may include additional components (e.g., acoustic filters and other components) that are not shown in FIG. 4.

One or more processors 420B may exchange information via tether 410 with behind-ear portion 406. One or more processors 420B may receive information from behind-ear portion 406 via tether 410 and perform an operation in response. Likewise, one or more processors 420B may transmit information to behind-ear portion 406 via tether 410 to cause behind-ear portion 406 to perform an operation in response.

For example, processors 420B may receive an indication of an audio data stream being output from behind-ear portion 406 and in response, cause output components 428B to produce audible sound representative of the audio stream. In another example, a biometric sensor of input components 426B may detect a physiological condition (e.g., heart rate, body temperature, blood sugar level, or other physiological condition) or a movement sensor of input components 426B may detect a change in movement (e.g., a change in biometric pressure, an acceleration, or other change in movement). Processors 420B may send an indication of the physiological condition or change in movement via tether 410 to behind-ear portion 406 for further processing, such as for executing a fall-detection algorithm, determining a user's health, detecting a three-dimensional gesture (e.g., a head shake or head nod), or performing some other operation based on data received from in-ear portion 408.

Ear-wearable device 400 may send information (e.g., via behind-ear portion 406) to accessory devices 104, such as portable case 204 of FIG. 2 and accessory device 300 of FIG. 3, for further processing, thus (indirectly) expanding the processing capabilities of ear-wearable device 400. And as described above, accessory devices (e.g., portable case 200, accessory device 300, etc.) may provide additional offline processing on behalf of ear-wearable device 400 by utilizing a cloud-based service or relying on assistance from one of computing devices 108 that is coupled to network 106.

In addition to the components described above, ear-wearable device 400 includes energy storage 436B. In some examples, energy storage 436B enables in-ear portion 408 to operate as a stand-alone hearing instrument without being operatively coupled to tether 410 and behind-ear portion 406. For example, a user may prefer to normally wear tether 410 and portions 406 and 408 during everyday use. However, when a user prefers to go without behind-ear portion 406 and tether 410 (e.g., for aesthetic reasons, when exercising, when working, or at any other time a user chooses to only wear in-ear portion 408), energy storage 436B provides sufficient electrical energy storage to power in-ear portion 408 during such times. Energy storage 436B may not be intended to provide sufficient electrical energy for all-day use of in-ear portion 408; rather energy storage 436B may provide one or more hours of use without altering the form-factor of in-ear portion 408 that enables in-ear portion 408 to be concealed in a user's ear canal.

Behind-ear portion 406 is a part of ear-wearable device 400 responsible for supporting in-ear portion 408 in outputting sound for hearing. In some examples, behind-ear portion 406 includes some or all of the components of in-ear portion 408 shown in FIG. 4. Behind-ear portion 406 may include some of the components and perform some of the functionality attributed to in-ear portion 408 in the above description, for example, to reduce a physical size of in-ear portion 408 or otherwise reduce complexity of in-ear portion 408. For example, in-ear portion 408 may support autonomous functionality (e.g., by operating independent of behind-ear portion 406 and tether 410). In such an example, in-ear portion 408 includes tether connections and some or all of the components shown in FIG. 4 including an energy source as shown in FIG. 4. In some examples, in-ear portion 408 includes additional memory for storing user data.

In the example of FIG. 4, behind-ear portion 406 includes one or more processors 420A, system charger 432, one or more output components 428A, one or more input components 426A, energy storage 436A. Behind-ear portion 406 further includes, in this example, one or more antennas 424, one or more communication units 438, data storage device 430, and communication bus 440. Within data storage device 430 are one or more application modules 444 and user data store 446.

In some examples, behind-ear portion 406 is configured as a detachable, modular component that houses a rechargeable energy source. For example, system charger 432 may include an electromagnetic transducer that is completely or partially contained within, or on, a housing of behind-ear portion 406 for receiving electrical energy for purposes of charging energy source 436A. System charger 432 may include an inductive charging coil, or antenna with a pulse width modulation integrated circuit (PWMIC) and/or rectifier. System charger 432 may be configured to receive electrical energy when behind-ear portion 406 mates with a charging retention structure of portable cases 104, 204, and 304 and store the received electrical energy in energy storage 436A.

In addition to providing electrical energy, the components of behind-ear portion 406 may further configure portion 406 to perform various other advanced functions. These other advanced functions include advanced battery functions such as, but not limited to: short-circuit protection, polarity detection, charging status or alerts, storage reserve capacity, graceful power shutdown, emergency power conservation mode, fast-charging options, and other advanced battery functions. For example, one of application modules 444, executing at processors 420A, may receive information from system charger 432 or directly from energy storage 436A and cause processors 420A to present, based on the received information, battery health and status information via a user interface provided by behind-ear portion 406, and/or the user interface provided by accessory devices 104.

The user interface provided by behind-ear portion 406 may present an audible or haptic type user interface to the user relying on output components 428A and/or output components 428B of in-ear portion 408. For instance, processors 420A may send data to processors 420B that cause processors 420B to use output components 428B to generate sounds, audible cues, haptic feedback, or other alerts regarding information such as, battery health, battery life, time remaining, storage reserve or capacity, health information of user 105, or other information. In reverse, a user interface provided by behind-ear portion 406 may receive commands from the user by relying on input components 426A and/or input components 426B of in-ear portion 408. For instance, processors 420A may receive data from processors 420B indicative of sounds, audible cues, or other information received by input components 426B as a user interacts with the user interface. Processors 420A may perform operations or alter the user interface based on the data received from processors 420B.

Other functions that may be provided by ear-wearable device 400 (e.g., behind-ear portion 406 of ear-wearable device 400), in various examples, include communication functions enabled by communication units 438 and antennas 424. Behind-ear portion 406 may enable in-ear portion 408 to communicate with external devices, such as computing devices 101, in addition to enabling communication with other hearing instruments. For example, one of application modules 444 (e.g., a media playback application) executing at processors 420A may receive an encoded audio stream from one of accessory devices 104, convert the encoded audio stream to a different format that is suitable for consumption by in-ear portion 408, and cause processors 420A to send the converted audio stream to processors 420B of in-ear portion 408 for subsequent decoding and playback to a user. Alternatively, one of application modules 444 may receive an encoded audio stream from in-ear portion 408, convert the encoded audio stream to a different format that is suitable for consumption by computing devices 101, and cause processors 420A to send the converted audio stream, via communication units 438, to computing devices 101 or portable cases 104, 204, or 304. In this way, in-ear portion 408 and behind-ear portion 406 can communicate together and with other hearing instruments using more reliable intra or inter body network protocols while simultaneously supporting communication outside the body using cellular, LTE, Bluetooth®, Wi-FI®, and other communication protocols that are supported by external devices, such as computing devices 101.

Other functionality provided by behind-ear portion 406 includes operating in a second mode when not being worn by a user (e.g., not tethered to in-ear portion 408) that is different than the mode behind-ear portion 406 operates-in when being word by the user. For example, processors 420A may detect when behind-ear portion 406 is detached from tether 410. In response to detecting that tether 410 is not operatively coupled to behind-ear portion 406, one of application modules 444 may cause processors 420A to perform autonomous functions, such as operating as a miniature multi-functional hearing assistance device accessory. In such a mode, behind-ear portion 406 may configure input components 426A to act as a wireless, remote microphone, or may configure communication units 438 to extend the range of communication signals being transmitted or received by portable cases 104, 204, and 304, in-ear portion 408, or one of external computing devices 101. In some examples, even though tether 410 may be removed from behind-ear portion 406, behind-ear portion 406 may still maintain a wireless communication connection with in-ear portion 408. Specifically, while operating in the second mode, a communication unit and/or antenna of in-ear portion 408 (not shown in FIG. 4) may wirelessly exchange communication signals with antennas 424 and communication units 438 of behind-ear portion 406, e.g., to transmit data representative of audio received by a microphone associated with behind-ear portion 406 to in-ear portion 408. As an illustration, the user may remove the behind-ear portion 406 and place it proximate to another person to capture speech emitted by the person for transmission to the in-ear portion 408, facilitating better conversational hearing, e.g., in a noisy environment.

As another example, when operating in the second mode when not being worn, behind-ear portion 406 may configure processors 420A to operate as a wireless audio controller that enables indirect, wireless pairing of in-ear portion 408 to portable cases 104, 204, and 304, in-ear portion 408, or one of external computing devices 101. By relying on behind-ear portion 406 for audio controller functions, in-ear portion 408 may offload connection management processing that in-ear portion 408 might otherwise be required to perform to communicate wirelessly with other devices, and as such, may reduce the rate of power consumption by in-ear portion 408 and thereby extend the energy reserve of energy storage 436B.

In any case, behind-ear portion 406 may perform the operations described herein while behind-ear portion 406 charges energy storage 436A from inside portable case 204. Likewise, behind-ear portion 406 may perform the operations described herein while behind-ear portion 406 is no longer charging and/or is located outside portable case 204.

Figure 5:
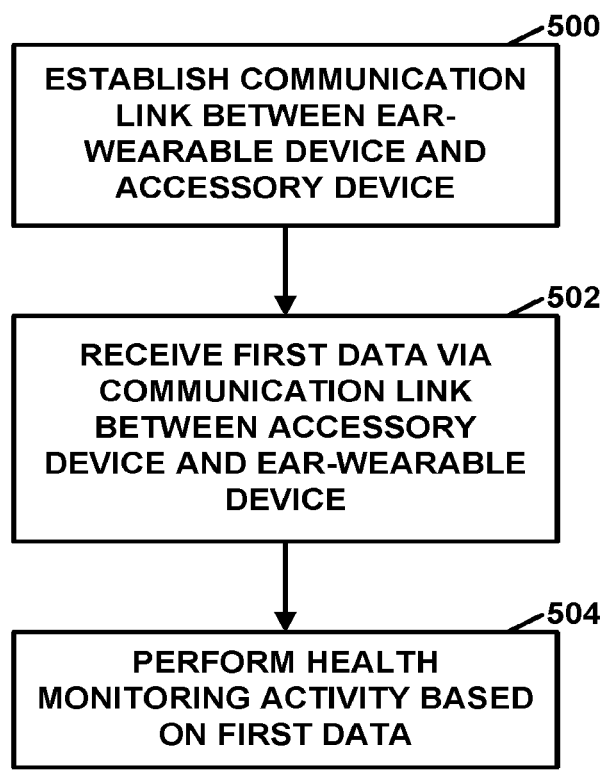
FIG. 5 is a flowchart illustrating an example operation of ear-wearable device(s) in accordance with a technique of this disclosure.

FIG. 5 is a flowchart illustrating an example operation of ear-wearable device(s) 104 in accordance with a technique of this disclosure. The flowcharts of this disclosure are provided as examples. Other examples may include more, fewer, or different actions.

In the example of FIG. 5, each accessory device in a set of accessory device(s) 104 (FIG. 1) may establish a respective communication link between the accessory device and an ear-wearable device (500). Accessory device(s) 104 do not need to establish or maintain the communication links concurrently. For each respective accessory device, the respective communication link may be a wireless communication link in which the respective accessory device receives radio signals generated by the ear-wearable device, an optical communication channel in which the respective accessory device receives light generated by the ear-wearable device, or an electrical communication channel in which the respective accessory device receives electrical pulses generated by the ear-wearable device. For instance, in the example of FIG. 2, portable case 204 may establish a communication channel with ear-wearable devices via a direct electrical contact or induction. In one example, a particular accessory device in the set of accessory devices 104 is a charging device, the communication link between the particular accessory device and the ear-wearable device is a charging device communication link, and the charging device may establish the charging device communication link at or during a time that the charging device is recharging the power source of the ear-wearable device. The charging device communication link is a communication link between the charging device and the ear-wearable device. The charging device communication link may be any of the wired or wireless communication links described elsewhere in this disclosure.

Furthermore, a particular accessory device in the set of accessory device(s) 104 may receive first data via the communication link between the particular accessory device and the ear-wearable device (502). For instance, the particular accessory device may receive a wireless transmission of the first data from the ear-wearable device. The particular accessory device may be any type of accessory device, such as a charging device adapted to recharge a power source of the ear-wearable device. In another example, the particular accessory device is a media streamer device configured to receive media data from a source device (e.g., a mobile telephone of user 105, a television, etc.) and wirelessly stream the media data to the ear-wearable device. In another example, the particular accessory device is a remote-control device configured to wirelessly control ear-wearable device(s) 102.

The first data may comprise information generated based on sensor signals from sensors that monitor user 105 of ear-wearable device(s) 102. Such sensor signals may include signals generated by sensors in sensor devices 110 and/or sensors in ear-wearable device(s) 102.

Accessory devices 104 may perform a health monitoring activity based on the first data (504). For instance, in an example where the particular accessory device is a charging device, the charging device may perform the health monitoring activity. In some examples, accessory devices 104 may communicate with each other to perform health monitoring activities. For instance, in one example, a first accessory device may receive first data from the ear-wearable device and generate second data based on the first data. In this example, the second data may include the first data or the second data may be the result of transforming or processing the first data in some way. Furthermore, in this example, the first accessory device may send the second data to a second accessory device in the set of accessory devices 104. In this example, the second accessory device may perform the health monitoring activity based on the second data.

In some examples, an accessory device may perform health monitoring activities based on a combination of data received by another accessory device and data received from ear-wearable device(s) 102. For instance, continuing the example of the previous paragraph, the second accessory device may receive third data from the ear-wearable device via the communication link between the second accessory device and the ear-wearable device. In this example, the second accessory device may perform the health monitoring activity based on the second data and the third data. For instance, in one example, the second data may include heart rhythm data and the third data may include data indicating the posture of user 105. In this example, the accessory device may provide both the heart rhythm data and the data indicating the posture of user 105 into a neural network that determines whether user 105 is experiencing a serious cardiac arrhythmia. In other examples, accessory devices 104 may send, via communication network 106, the first data to a computing device (e.g., one of computing devices 108) and may receive second data from the computing device where the second data is based on the first data. In this example, accessory devices 104 may cause ear-wearable device(s) 102 to generate an audio notification based on the second data.

Examples of health monitoring activities are described elsewhere in this disclosure. For example, accessory devices 104 may cause ear-wearable device(s) 102 to generate an audio notification related to the user's health. For example, accessory devices 104 may send audio data to ear-wearable device(s) 102 for playback by ear-wearable device(s) 102. In another example, accessory devices 104 may send a code to ear-wearable device(s) 102 that indicates to ear-wearable device(s) 102 to playback audio data stored on one or more of ear-wearable device(s) 102.

In some examples, the health monitoring activity is performed in part by one or more of computing devices 108. Thus, in some examples, accessory device(s) 104 may send, via communication network 106, the first data to a computing device (e.g., computing device 108A) that is configured to perform a health monitoring activity, such as providing data based on the first data to a party other than user 105.

In some examples of this disclosure, ear-wearable device(s) 102 may perform some health monitoring activities of health monitoring system 100. However, it may be desirable to perform a richer set of health monitoring activities than can be reasonably performed on ear-wearable device(s) 102, given the limited power and computational resources of ear-wearable device(s) 102. Hence, in accordance with a technique of this disclosure, ear-wearable device(s) 102 may triage which information needs to be sent to accessory devices 104. If it is critical to send information to monitoring nodes of health monitoring system 100 (e.g., accessory devices 104 or computing devices 108), ear-wearable device(s) 102 may immediately establish a wireless communication session with an accessory device. Otherwise, ear-wearable device(s) 102 may wait to send data to accessory devices 104.

Figure 6:
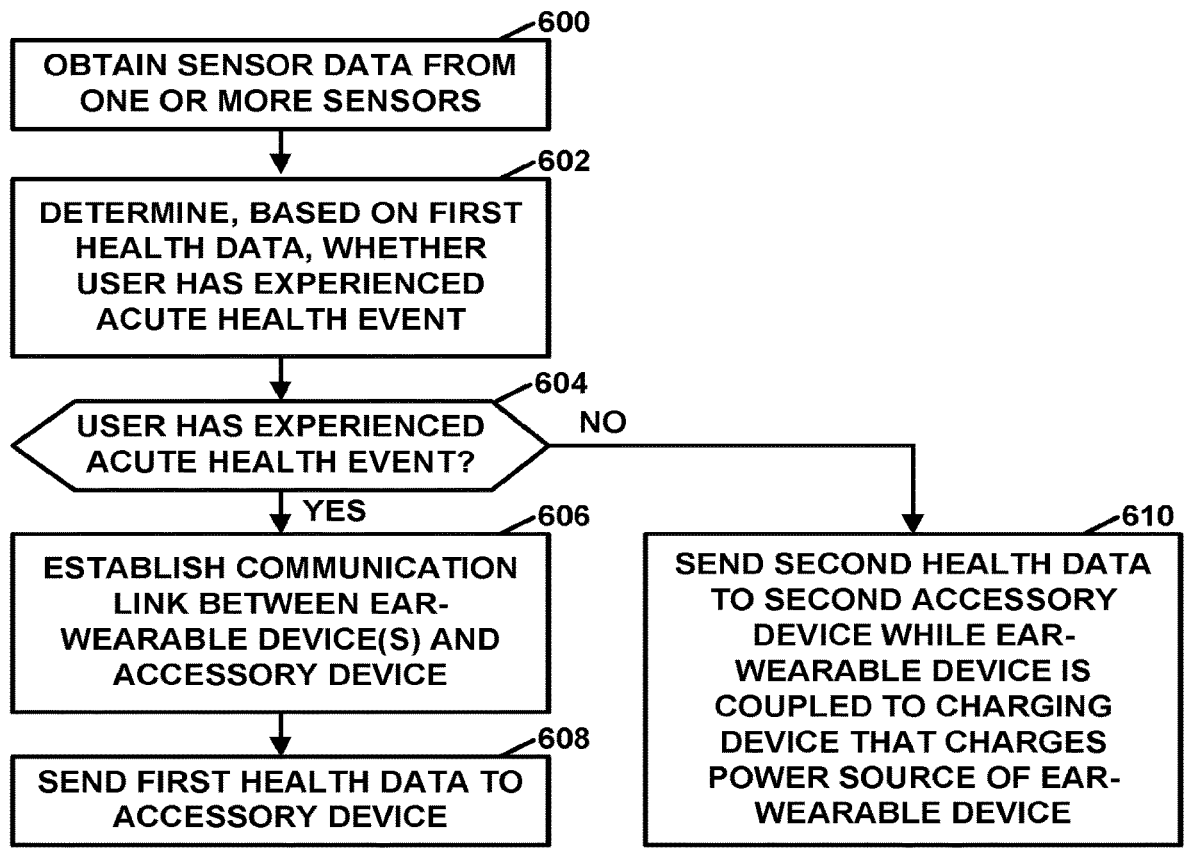
FIG. 6 is an example of an information triage operation of an ear-wearable device in accordance with a technique of this disclosure.

FIG. 6 is an example of an information triage operation of an ear-wearable device in accordance with a technique of this disclosure. In the example of FIG. 6, ear-wearable device(s) 102 may obtain sensor data from one or more sensors configured to gather information about user 105 of ear-wearable device(s) 102 (600). For example, ear-wearable device(s) 102 may obtain sensor data from sensors in ear-wearable device(s) 102 and/or sensor devices 110.

Furthermore, in the example of FIG. 6, ear-wearable device(s) 102 may determine, based on the sensor data, whether user 105 has experienced an acute health event (602). For example, ear-wearable device 102 may determine, based on the sensor data, that user 105 has fallen, that user 105 is experiencing a heart arrhythmia, that user 105 is having a seizure or about to have a seizure, that user 105 has a dangerous fever, that user 105 is experiencing heatstroke or hypothermia, that user 105 has dangerously high or low blood pressure, or that user 105 is experiencing another type of acute health event.

In response to determining that user 105 has experienced an acute health event ("YES" branch of 604), ear-wearable device(s) 102 may establish a communication link between ear-wearable device(s) 102 and a first accessory device of the set of accessory devices 104 (606). For example, the communication link may be a wireless communication link in which the first accessory device receives wireless signals generated by ear-wearable device(s) 102. Ear-wearable device(s) 102 may establish the communication link immediately in response to determining that user 105 has experienced the acute health event. In some examples, ear-wearable device(s) 102 may use increasing power levels of wireless signals to help ensure that at least one of accessory devices 104 is able to receive the wireless signals. In this example, the first accessory device may be that one of accessory device(s) 102 that first responds to the wireless signals generated by ear-wearable device(s) 102.

Ear-wearable device(s) 102 may send first health data to the first accessory device via the communication link (608). The first health data is based on the sensor data. In some examples, the first health data may be or comprise the sensor data itself. In some examples, the first health data may include data generated by ear-wearable device(s) 102 such as an indication of the acute health condition along with, in some examples, supporting data. Monitoring nodes of health monitoring system 100 (e.g., the accessory device, other ones of accessory devices 104, and/or computing devices 108) may use the first health data to perform various health monitoring activities, such as alerting one or more third parties, causing ear-wearable device(s) 102 to output audible instructions or alerts, and so on.

However, in response to determining that user 105 has not experienced the acute health event ("NO" branch of 604), ear-wearable device(s) 102 may send second health data based on the sensor data to a second accessory device while one or more of ear-wearable device(s) 102 are coupled to a charging device that charges a power source of the ear-wearable device (610). Thus, ear-wearable device(s) 102 may be able to provide the second data at a time when transmitting the second data would not negatively impact the amount of power stored in the power source(s) of ear-wearable device(s) 102. In some examples, the charging device is the second accessory device. The first accessory device and the second accessory device may be the same device. In some examples, the second data is the same as the first data. In other examples, the second data may include more or different data than the first data. For instance, the second data may include data that is not critical the user's immediate health, such as the number of steps that user 105 has taken during a given time period. In other examples, ear-wearable device(s) 102 may send the second data to the second accessory device under other conditions. Such other conditions may include instances in which ear-wearable device(s) 102 are able to communicate with the second accessory device using a low-power wireless communication technology, such as BTE.

In some examples, the definition of the acute health event may be customized to user 105. In other words, what might be an acute health event for one user might not be for another user. For instance, low blood glucose may not be critical for a non-diabetic person but might be for a diabetic person. Accordingly, in ear-wearable device(s) 102 may receive configuration data. Ear-wearable device(s) 102 may customize a definition of the acute health event to user 105 of ear-wearable device(s) 102 based on the configuration data.

Furthermore, as discussed above, in some examples, user 105 may initiate monitoring of one or more aspects of the health of user 105. In the context of FIG. 6, ear-wearable device(s) 102 may, in response to input from user 105, send health data to one or more of accessory devices 104. The health data may be based on the sensor data. For instance, the health data may receive data from one or more of accessory devices 104. The received data may be based on the sent data and may provide information regarding a health condition of user 105.

The following paragraphs provide a non-limiting set of examples. These and other examples are within the scope of this disclosure.

Example 1A. A method of health monitoring, the method comprising: establishing, by each accessory device in a set of accessory devices, a respective communication link between the accessory device and an ear-wearable device, the respective communication link being: a wireless communication link in which the accessory device receives radio signals generated by the ear-wearable device, an optical communication channel in which the accessory device receives light generated by the ear-wearable device, or an electrical communication channel in which the accessory device receives electrical pulses generated by the ear-wearable device; receiving, by a particular accessory device in the set of accessory devices, first data via the communication link between the particular accessory device and the ear-wearable device, the first data comprising information generated based on sensor signals from sensors that monitor a user of the ear-wearable device; and performing, by the set of accessory devices, a health monitoring activity based on the first data.

Example 2A. The method of example 1A, wherein receiving the first data comprises receiving, by the particular accessory device, a wireless transmission of the first data from the ear-wearable device.

Example 3A. The method of any of examples 1A-2A, wherein the particular accessory device is a charging device adapted to recharge a power source of the ear-wearable device.

Example 4A. The method of example 3A, wherein: the communication link between the particular accessory device and the ear-wearable device is a charging device communication link, and establishing the charging device communication link comprises establishing, by the charging device, the charging device communication link at or during a time that the charging device is recharging the power source of the ear-wearable device.

Example 5A. The method of any of examples 3A-4A, wherein the charging device performs the health monitoring activity.

Example 6A. The method of any of examples 1A-5A, wherein: the particular accessory device is a first accessory device, the method further comprises: generating, by the first accessory device, second data based on the first data; sending, by the first accessory device, the second data to a second accessory device in the set of accessory devices, and performing the health monitoring activity comprises performing, by the second accessory device, the health monitoring activity based on the second data.

Example 7A. The method of example 6A, wherein: the method further comprises receiving, by the second accessory device, third data from the ear-wearable device via the communication link between the second accessory device and the ear-wearable device, and performing the health monitoring activity comprises performing, by the second accessory device, health monitoring activity based on the second data and the third data.

Example 8A. The method of any of examples 1A-2A and 6A-7A, wherein the particular accessory device is a media streamer device configured to receive media data from a source device and wirelessly stream the media data to the ear-wearable device.

Example 9A. The method of example 8A, wherein the source device is a mobile telephone of the user of the ear-wearable device.

Example 10A. The method of any of examples 1A-2A and 6A-7A, wherein the particular accessory device is a remote-control device configured to wirelessly control the set of ear-wearable devices.

Example 11A. The method of any of examples 1A-10A, further comprising: sending, by the accessory devices, via a communication network, the first data to a computing device that is configured to provide third data based on the second data to a party other than the user of the ear-wearable device.

Example 12A. The method of any of examples 1A-11A, further comprising: sending, by the one or more accessory devices in the set of accessory devices, via a communication network, the first data to a computing device; receiving, by the accessory devices, second data from the computing device, wherein the second data is based on the first data; and causing, by the accessory devices, the ear-wearable device to generate an audio notification based on the second data.

Example 13A. The method of any of examples 1A-12A, further comprising: determining, by the accessory devices, that the ear-wearable device is no longer within wireless communication range of any of the accessory devices; in response to determining that the ear-wearable device is no longer within wireless communication range of any of the accessory devices, triggering, by the accessory devices, a computing device to generate an alert to a party other than the user of the ear-wearable device.

Example 14A. The method of any of examples 1A-13A, further comprising causing, by the accessory devices, the ear-wearable device to generate an audio notification related to the user's health.

Example 15A. The method of any of examples 1A-14A, wherein: the set of accessory devices includes a plurality of accessory devices and the communication links between the plurality of accessory devices and the ear-wearable device are wireless communication links; estimating, by the accessory devices, based on wireless signals emitted by the ear-wearable device and detected by the accessory devices, a location of the ear-wearable device; and sending, by the accessory devices, navigation information to a computing device, the navigation information indicating the estimated location of the ear-wearable device.

Example 16A. The method of any of examples 1A-15A, wherein at least one of: one or more of the accessory devices is designed specifically for use as an accessory to the ear-wearable device, the particular accessory device is designed specifically for use as an accessory to the ear-wearable device, or each of the accessory devices is designed specifically for use as an accessory to the ear-wearable device.

Example 1B. An accessory device comprising: one or more communication units configured to: establish a communication link between the accessory device and an ear-wearable device, the communication link being: a wireless communication link in which the accessory device receives radio signals generated by the ear-wearable device, an optical communication channel in which the accessory device receives light generated by the ear-wearable device, or an electrical communication channel in which the accessory device receives electrical pulses generated by the ear-wearable device; and receive first data via the communication link between the accessory device and the ear-wearable device, the first data comprising information generated based on sensor signals from sensors that monitor a user of the ear-wearable device; and one or more processors configured to perform a health monitoring activity based on the first data.

Example 2B. The accessory device of example 1B, wherein the one or more communication units are configured to receive a wireless transmission of the first data from the ear-wearable device.

Example 3B. The accessory device of any of examples 1B-2B, wherein the accessory device is a charging device adapted to recharge a power source of the ear-wearable device.

Example 4B. The accessory device of example 3B, wherein: the communication link between the particular accessory device and the ear-wearable device is a charging device communication link, and the one or more communication units are configured to establish the charging device communication link at or during a time that the charging device is recharging the power source of the ear-wearable device.

Example 5B. The accessory device of any of examples 1B-4B, wherein: the one or more processors are configured to generate second data based on the first data, and the one or more communication units are configured to send the second data to a second accessory device in a set of accessory devices, the second accessory device configured to perform a second health monitoring activity based on the second data.

Example 6B. The accessory device of any of examples 1B-5B, wherein: the one or more communication units are further configured to receive second data from a second accessory device via a communication link between the accessory device and the second accessory device, and the one or more processors are configured to perform the health monitoring activity based on the first data and the second data.

Example 7B. The accessory device of any of examples 1B-2B and 5B-6B, wherein the accessory device is a media streamer device configured to receive media data from a source device and wirelessly stream the media data to the ear-wearable device.

Example 8B. The accessory device of example 7B, wherein the source device is a mobile telephone of the user of the ear-wearable device.

Example 9B. The accessory device of any of examples 1B-2B and 5B-6B, wherein the accessory device is a remote-control device configured to wirelessly control the set of ear-wearable devices.

Example 10B. The accessory device of any of examples 1BA-9B, wherein the one or more communication units are configured to send, via a communication network, the first data to a computing device that is configured to provide second data based on the first data to a party other than the user of the ear-wearable device.

Example 11B. The accessory device of any of examples 1B-10B, wherein: the one or more communication units are configured to: send, via a communication network, the first data to a computing device; and receive second data from the computing device, wherein the second data is based on the first data; and the one or more processors are configured to cause the ear-wearable device to generate an audio notification based on the second data.

Example 12B. The accessory device of any of examples 1B-11B, wherein the one or more processors are configured to: determine that the ear-wearable device is no longer within wireless communication range of any of the accessory devices; in response to determining that the ear-wearable device is no longer within wireless communication range of any of the accessory devices, trigger a computing device to generate an alert to a party other than the user of the ear-wearable device.

Example 13B. The accessory device of any of examples 1B-12B, wherein the one or more processors are further configured to cause the ear-wearable device to generate an audio notification related to the user's health.

Example 14B. The accessory device of any of examples 1B-13B, wherein: a plurality of accessory devices includes the accessory device; the one or more processors are configured to estimate, based on wireless signals emitted by the ear-wearable device and detected by one or more of the accessory devices, a location of the ear-wearable device; and the one or more communication units are configured to send navigation information to a computing device, the navigation information indicating the estimated location of the ear-wearable device.

Example 15B. The accessory device of any of examples 1B-14B, wherein the accessory device is designed specifically for use as an accessory to the ear-wearable device.

Example 1C. An accessory device comprising: means for establishing a communication link between the accessory device and an ear-wearable device, the communication link being a wireless communication link in which the accessory device receives radio signals generated by the ear-wearable device, an optical communication channel in which the accessory device receives light generated by the ear-wearable device, or an electrical communication channel in which the accessory device receives electrical pulses generated by the ear-wearable device; means for receiving first data via the communication link between the accessory device and the ear-wearable device, the first data comprising information generated based on sensor signals from sensors that monitor a user of the ear-wearable device; and means for performing a health monitoring activity based on the first data.

Example 2C. The accessory device of example 1C, further comprising means for performing the methods of any of examples 2A-16A.

Example 1D. A computer-readable storage medium having instructions that cause a set of accessory devices to: establish, by each accessory device in the set of accessory devices, a respective communication link between the accessory device and an ear-wearable device, the respective communication link being: a wireless communication link in which the accessory device receives radio signals generated by the ear-wearable device, an optical communication channel in which the accessory device receives light generated by the ear-wearable device, or an electrical communication channel in which the accessory device receives electrical pulses generated by the ear-wearable device; receive, by a particular accessory device in the set of accessory devices, first data via the communication link between the particular accessory device and the ear-wearable device, the first data comprising information generated based on sensor signals from sensors that monitor a user of the ear-wearable device; and perform, by the set of accessory devices, a health monitoring activity based on the first data.

Example 2D. The computer-readable storage medium of example 1D, wherein execution of the instruction further causes the accessory devices to perform the methods of any of examples 2A-16A.

Example 1E. A method comprising: obtaining, by an ear-wearable device, sensor data from one or more sensors configured to gather information about a user of the ear-wearable device; determining, by the ear-wearable device, based on the sensor data, whether the user has experienced an acute health event; in response to determining that the user has experienced an acute health event: establishing, by the ear-wearable device, a communication link between the ear-wearable device and a first accessory device, the communication link being a wireless communication link in which the accessory device receives wireless signals generated by the ear-wearable device; and sending, by the ear-wearable device, first health data to the first accessory device via the communication link, the first health data being based on the sensor data; and in response to determining subsequently that the user has not experienced the acute health event, sending, by the ear-wearable device, second health data based on the sensor data to a second accessory device while the ear-wearable device is coupled to a charging device that charges a power source of the ear-wearable device.

Example 2E. The method of example 1E, wherein the second accessory device is the charging device.

Example 3E. The method of any of examples 1E-2E, wherein the second accessory device is the first accessory device.

Example 4E. The method of any of examples 1E-3E, wherein the second health data comprises the first health data.

Example 5E. The method of any of examples 1E-4E, further comprising: receiving, by the ear-wearable device, configuration data; and customizing, by the ear-wearable device, a definition of the acute health event to the user of the ear-wearable device based on the configuration data.

Example 6E. The method of any of examples 1E-6E, further comprising: in response to input from the user, sending, by the ear-wearable device, second health data based on the sensor data to the accessory devices; and receiving, by the ear-wearable device, third data from the accessory device, the third data being based on the second data and providing information regarding a health condition of the user.

Example 1F. An ear-wearable device comprising: one or more communication units; and one or more processors configured to: obtain sensor data from one or more sensors configured to gather information about a user of the ear-wearable device; determine, based on the sensor data, whether the user has experienced an acute health event; wherein the one or more communication units are configured to: in response to determining that the user has experienced an acute health event: establish a communication link between the ear-wearable device and a first accessory device, the communication link being a wireless communication link in which the accessory device receives wireless signals generated by the ear-wearable device; and send first health data to the first accessory device via the communication link, the first health data being based on the sensor data; and in response to determining that the user has not experienced the acute health event, send second health data based on the sensor data to a second accessory device while the ear-wearable device is coupled to a charging device that charges a power source of the ear-wearable device.

Example 2F. The ear-wearable device of example 1F, wherein the second accessory device is the charging device.

Example 3F. The ear-wearable device of any of examples 1F-2F, wherein the second accessory device is the first accessory device.

Example 4F. The ear-wearable device of any of examples 1F-3F, wherein the second health data comprises the first health data.

Example 5F. The ear-wearable device of any of examples 1F-4F, wherein: the one or more communication units are configured to receive configuration data; and the one or more processors are configured to customize a definition of the acute health event to the user of the ear-wearable device based on the configuration data.

Example 6F. The ear-wearable device of any of examples 1F-6F, wherein the one or more communication units are configured to: in response to input from the user, send second health data based on the sensor data to the accessory devices; and receive third data from the accessory device, the third data being based on the second data and providing information regarding a health condition of the user.

Example 1G. An ear-wearable device comprising: means for obtaining sensor data from one or more sensors configured to gather information about a user of the ear-wearable device; means for determining, based on the sensor data, whether the user has experienced an acute health event; means for establishing, in response to determining that the user has experienced an acute health event, a communication link between the ear-wearable device and a first accessory device, the communication link being a wireless communication link in which the accessory device receives wireless signals generated by the ear-wearable device, and sending first health data to the first accessory device via the communication link, the first health data being based on the sensor data; and means for sending, in response to determining that the user has not experienced the acute health event, second health data based on the sensor data to a second accessory device while the ear-wearable device is coupled to a charging device that charges a power source of the ear-wearable device.

Example 2G. The ear-wearable device of example 1G, further comprising means for performing the methods of any of examples 2E-6E.

Example 1H. A computer-readable storage medium having instructions stored thereon that, when executed, cause an ear-wearable device to: obtain sensor data from one or more sensors configured to gather information about a user of the ear-wearable device; determine, based on the sensor data, whether the user has experienced an acute health event; in response to determining that the user has experienced an acute health event: establish a communication link between the ear-wearable device and a first accessory device, the communication link being a wireless communication link in which the accessory device receives wireless signals generated by the ear-wearable device; and send first health data to the first accessory device via the communication link, the first health data being based on the sensor data; and in response to determining subsequently that the user has not experienced the acute health event, send second health data based on the sensor data to a second accessory device while the ear-wearable device is coupled to a charging device that charges a power source of the ear-wearable device.

Example 2H. The computer-readable storage medium of example 1G, wherein execution of the instructions causes the ear-wearable device to perform the methods of any of examples 2E-6E.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection may be considered a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transitory, tangible storage media. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A method implemented by an ear-wearable device worn by a wearer, the method comprising:
   obtaining, by the ear-wearable device, sensor data from one or more sensors of the ear-wearable device;
   determining, by the ear-wearable device and based on the sensor data, if the wearer is experiencing an acute health event, the ear-wearable device storing configuration data comprising a definition of the acute health event customized for the wearer;
   establishing, by the ear-wearable device, a first communication link between the ear-wearable device and a first accessory device of a plurality of accessory devices in response to determining that the wearer is experiencing the acute health event;
   sending first health data from the ear-wearable device to the first accessory device via the first communication link, the first health data comprising data concerning the acute health event; and
   sending second health data based on the sensor data from the ear-wearable device to a second accessory device of the plurality of accessory devices via a second communication link in response to an absence of the wearer experiencing the acute health event.

2. The method of claim 1, wherein the second health data comprises data concerning the wearer distinct from the first health data.

3. The method of claim 1, comprising:
   receiving, by the ear-wearable device, the configuration data; and
   customizing, by the ear-wearable device, the definition of the acute health event based on the configuration data.

4. The method of claim 1, wherein the second health data is sent at a time when transmitting the second health data does not negatively impact an amount of power stored in a power source of the ear-wearable device.

5. The method of claim 1, wherein:
   the second accessory device comprises a charging device configured to charge the ear-wearable device; and
   the ear-wearable device sends the second health data to the charging device while the ear-wearable device is coupled to the charging device.

6. The method of claim 1, wherein the sensor data is further obtained from one or more body sensors.

7. The method of claim 1, further comprising receiving, by the ear-wearable device, third health data from the second accessory device, the third health data being based on the second health data and providing information regarding a health condition of the wearer.

8. The method of claim 1, comprising increasing a power level of wireless signals produced by the ear-wearable device to enhance reception of the wireless signals by at least one of the plurality of accessory devices in response to determining that the wearer is experiencing the acute health event.

9. The method of claim 1, comprising performing, by the first accessory device or a computing device communicatively coupled to the first accessory device, a health monitoring activity in response to receiving the first health data.

10. The method of claim 1, wherein the ear-wearable device generates an audio notification concerning the wearer's health in response to information received from the first accessory device.

11. An ear-wearable device configured to be worn by a wearer, comprising:
   one or more sensors;
   one or more communication units; and
   one or more processors configured to:
   obtain sensor data from the one or more sensors;
   determine, based on the sensor data, if the wearer is experiencing an acute health event, a memory of the ear-wearable device storing configuration data comprising a definition of the acute health event customized for the wearer;

establish a first communication link between the one or more communication units and a first accessory device of a plurality of accessory devices in response to determining that the wearer is experiencing the acute health event;

send first health data from the ear-wearable device to the first accessory device via the first communication link, the first health data comprising data concerning the acute health event; and send second health data based on the sensor data from the ear-wearable device to a second accessory device of the plurality of accessory devices via a second communication link in response to an absence of the wearer experiencing the acute health event.

12. The device of claim 11, wherein the second health data comprises data concerning the wearer distinct from the first health data.

13. The device of claim 11, wherein the one or more processors are configured to:
receive the configuration data; and
customize the definition of the acute health event based on the configuration data.

14. The device of claim 11, wherein the second health data is sent at a time when transmitting the second health data does not negatively impact an amount of power stored in a power source of the ear-wearable device.

15. The device of claim 11, wherein:
the second accessory device comprises a charging device configured to charge the ear-wearable device; and
the one or more processors are configured to send the second health data to the charging device while the ear-wearable device is coupled to the charging device.

16. The device of claim 11, wherein the sensor data is further obtained from one or more body sensors.

17. The device of claim 11, wherein the one or more processors are configured to receive third health data from the second accessory device, the third health data being based on the second health data and providing information regarding a health condition of the wearer.

18. The device of claim 11, wherein the one or more processors are configured to increase a power level of wireless signals produced by the one or more communication units to enhance reception of the wireless signals by at least one of the plurality of accessory devices in response to determining that the wearer is experiencing the acute health event.

19. The device of claim 11, wherein the first accessory device or a computing device communicatively coupled to the first accessory device is configured to perform a health monitoring activity in response to receiving the first health data.

20. The device of claim 11, wherein the one or more processors are configured to generate an audio notification concerning the wearer's health in response to information received from the first accessory device.

* * * * *